US012084505B2

(12) United States Patent
Boquet et al.

(10) Patent No.: US 12,084,505 B2
(45) Date of Patent: Sep. 10, 2024

(54) ANTIBODY AGAINST THE ENDOTHELIN RECEPTOR SUBTYPE A, AND USES THEREOF

(71) Applicants: COMMISSARIAT A L'ENERGIE ATOMIQUE ET AUX ENERGIES ALTERNATIVES, Paris (FR); Universite de Paris, Paris (FR); UNIVERSITE DE MONTPELLIER, Montpellier (FR); Institut National de la Sante et de la recherche Medicale, Paris (FR)

(72) Inventors: Didier Boquet, Les Pavillons sous Bois (FR); Amaury Herbet, Courbevoie (FR); Frederic Ducancel, Longjumeau (FR); Narciso Costa, Saulx-les-Chartreux (FR); Jean-Yves Couraud, Paris (FR); Jean-Philippe Hugnot, Montpellier (FR)

(73) Assignees: COMMISSARIAT A L'ENERGIE ATOMIQUE ET AUX ENERGIES ALTERNATIVES, Paris (FR); UNIVERSITÉ PARIS CITÉ, Paris (FR); UNIVERSITE DE MONTPELLIER, Montpellier (FR); Institut National de la Sante et de la recherche Medicale, Paris (FR)

( * ) Notice: Subject to any disclaimer, the term of this patent is extended or adjusted under 35 U.S.C. 154(b) by 542 days.

(21) Appl. No.: 16/967,763

(22) PCT Filed: Feb. 4, 2019

(86) PCT No.: PCT/FR2019/050245
§ 371 (c)(1),
(2) Date: Aug. 6, 2020

(87) PCT Pub. No.: WO2019/155151
PCT Pub. Date: Aug. 15, 2019

(65) Prior Publication Data
US 2022/0089755 A1 Mar. 24, 2022

(30) Foreign Application Priority Data
Feb. 7, 2018 (FR) ..................................... 1851026

(51) Int. Cl.
*G01N 33/74* (2006.01)
*C07K 16/28* (2006.01)
*G01N 33/574* (2006.01)

(52) U.S. Cl.
CPC ... *C07K 16/2869* (2013.01); *G01N 33/57407* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| 4,816,567 A | 3/1989 | Cabilly et al. |
| 2018/0256714 A1 | 9/2018 | Zhang et al. |

FOREIGN PATENT DOCUMENTS

| CA | 2 971 491 A1 | 6/2017 |
| CN | 103728454 A | 4/2014 |
| WO | WO 2007/095353 A2 | 8/2007 |
| WO | WO 2012/045776 A1 | 4/2012 |
| WO | WO 2017/220739 A1 | 12/2017 |

OTHER PUBLICATIONS

Paul, Fundamental Immunology, (textbook), 292-295, 1993.*
Rudikoff et al. (Proc. Natl. Acad. Sci. USA, 79: 1979-1983, 1982).*
Colman P. M. (Research in Immunology, 145:33-36, 1994).*
Brummell et al. (Biochemistry 32:1180-1187,1993).*
Jupp, PW, (Med Hypotheses 112: 18-23, 2018).*
Shergalis et al (Pharmacol Rev 70: 412-445, 2018).*
Winkles et al (BBRC 191: 1081-1088, 1993).*
MacCallum et al (J. Mol. Biol. 262: 732-745, 1996).*
DePascalis et al (J Immunol, 169: 3076-3084, 2002).*
Casset et al (BBRC, 307: 198-205, 2003).*
Ju et al (Exp Mol Med 53: 1437-1448, 2021) (Year: 2021).*
Bagnato et al (Am J Pathol 158: 841-847, 2001) (Year: 2001).*
Wulfing et al (Eur Urol 47: 593-600, 2005) (Year: 2005).*
Eberl et al (Brit J Cancer 88: 788-795, 2003) (Year: 2003).*
Bagnato et al (Can Res 59: 720-727, 1999) (Year: 1999).*
Yohn et al (BBRC 201: 449-457, 1994) (Year: 1994).*
Mangahas et al (J Invest Dermatol 123: 1135-1139, 2004) (Year: 2004).*
Borrull et al, (MABS 8: 1371-1385, 2016) (Year: 2016).*
International Search Report issued Oct. 31, 2019 in PCT/FR2019/050245 (submitting English translation only), 3 pages.
French Preliminary Search Report issued Jun. 4, 2018 in Patent Application No. FR 1851026 (with English translation of categories of cited documents), 2 pages.
Stuart Rudikoff, et al., "Single Amino Acid Substitution Altering Antigen-Binding Specificity" Proceedings of the National Academy of Sciences (PNAS), USA, vol. 79, XP007901436, Mar. 1, 1982, pp. 1979-1983.
A. Herbet et al. "Antibodies Targeting Human Endothelin-1 Receptors Reveal Different Conformational States in Cancer Cells" Physiological Research, XP055635431, May 6, 2018, pp. S257-S264.
Sebastien Bulenger, et al, "Emerging Role of Homo- and Heterodimerization in G-Protein-coupled Receptor Biosynthesis and Maturation" Trends in Pharmacological Sciences, vol. 26, No. 3, Mar. 2005, pp. 131-137.

(Continued)

*Primary Examiner* — Kimberly Ballard
*Assistant Examiner* — Aditi Dutt
(74) *Attorney, Agent, or Firm* — Oblon, McClelland, Maier & Neustadt, L.L.P.

(57) ABSTRACT

The present invention relates to antibodies against the endothelin receptor subtype A, in particular monoclonal antibodies, fragments or derivatives thereof. The present invention also relates to the therapeutic or diagnostic use of this antibody or as a research tool in the field of cancers, in particular glioblastoma.

17 Claims, 8 Drawing Sheets

Specification includes a Sequence Listing.

(56) References Cited

OTHER PUBLICATIONS

Terry Kenakin, et al., "Seven Transmembrane Receptors as Shapeshifting Proteins: The Impact of Allosteric Modulation and Functional Selectivity on New Drug Discovery" Pharmacological Review, vol. 62, 2010, pp. 265-304.

Daniel Hilger, et al, "Structure and Dynamics of GPCR Signaling Complexes" Nature Structural & Molecular Biology, vol. 25, Jan. 2018, pp. 4-12.

Wataru Shihoya, et al, "Activation Mechanism of Endothelin $ET_B$ Receptor by Endothelin-1" Nature, vol. 537, Sep. 15, 2016, 23 pages.

Anna Bagnato, et al. "The endothelin axis in cancer" The International Journal of Biochemistry & Cell Biology, vol. 40, 2008, pp. 1443-1451.

Laura Rosanò, et al., "Endothelin 1 in Cancer: Biological Implications and Therapeutic Opportunities" Nature Reviews, Cancer, vol. 13, Sep. 2013, pp. 637-651.

Bertrand Allard, et al., "Generation and Characterization of Rendomab-B1, a Monoclonal Antibody Displaying Potent and Specific Antagonism of the Human Endothelin B Receptor" mAbs, vol. 5, Issue 1, Jan./Feb. 2013, pp. 56-69.

Aurelie Borrull, et al, "Rendomab B4, a Monoclonal Antibody that Discriminates the Human Endothelin B Receptor of Melanoma Cells and Inhibits their Migration" MABS, vol. 8, No. 7, 2016, pp. 1371-1385.

Sylvie Cazaubon, et al., "Endothéline-1 Angiotensine II et Cancer" Médecine/Sciences, vol. 22, No. 4, 2006, pp. 416-422 and cover page.

Rahman Shah, "Endothelins in Health and Disease" European Journal of Internal Medicine, vol. 18, 2007, pp. 272-282.

Soussan Irani, et al. "A Review of the Profile of Endothelin Axis in Cancer and its Management" Critical Reviews in Oncology/Hematology, vol. 89, No. 2, XP28817538, 2014, pp. 314-321.

Motohiro Kondoh, et al, "Isolation of Anti-Endothelin Receptor Monoclonal Antibodies for use in Receptor Characterization" Biochemical and Biophysical Research Communications, vol. 172, No. 2, Oct. 30, 1990, pp. 503-510.

Martine Verhoeyen et al, "Reshaping Human Antibodies: Grafting an Antilysozyme Activity" Science, vol. 239, 1988, pp. 1534-1536.

Tristan J. Vaughan, et al, "Human Antibodies by Design" Nature Biotechnology, vol. 16, Jun. 1998, pp. 535-539.

J. Sambrook, et al, "Molecular Cloning, a Laboratory Manual, Second Edition" Cold Spring Harbor Laboratory Press, 1989, 34 pages.

Giorgia Egidy et al, "The Endothelin System in Human Glioblastoma" Laboratory Investigation, J. Tech. Methods Pathol., vol. 80, No. 11, Nov. 2000, pp. 1681-1689.

\* cited by examiner

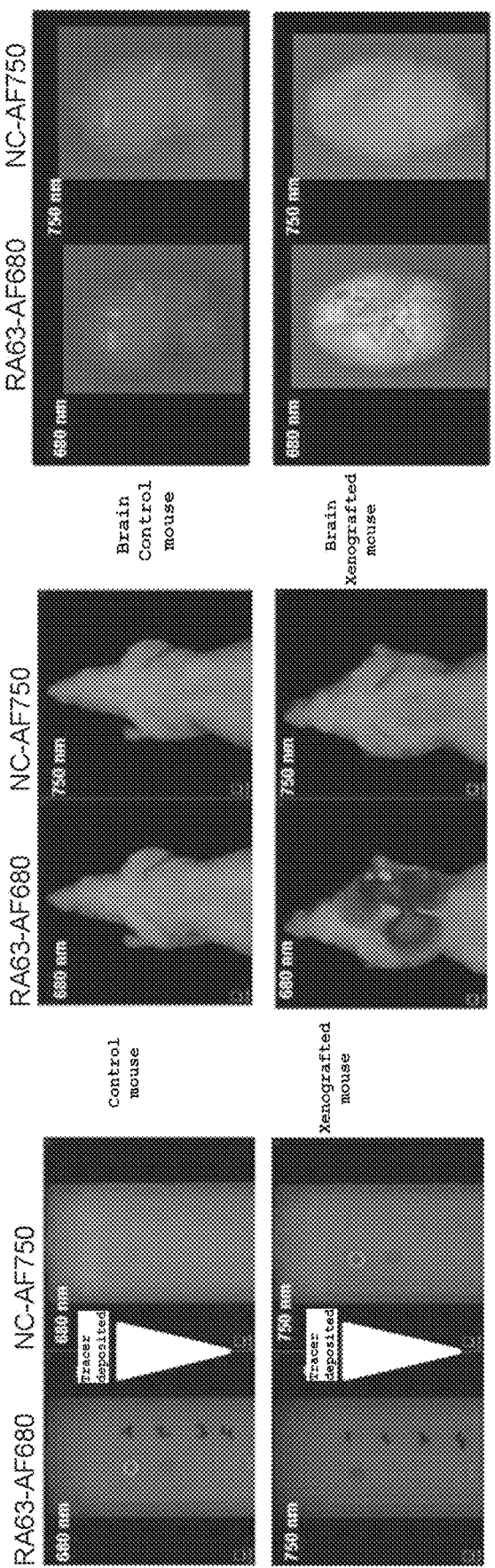

Sequences of the RA63 light chain

VLRendoMabA63 (nucleotide)

\>VLRendoMabA63 (SEQ ID NO: 11)
GATGTTTTGATGACCCAAACTCCACTCTCCCTGCCTGTCAGTCTTGGAGATCAAGCCTCCATCTC
GTGCAGATCTAGTCAGAGCATTGTATATAGTAATGGAAAAATCTATTTAGAATGGTACCTGCAGAA
ACCAGGCCAGTCTCCAAAGCTCCTAATCTACAAAGTTTCCAACCGATTTTCTGGGGTCCCAGACA
GGTTCAGTGGCAGTGGATCAGGGACAGATTTCACACTCAAGATCAGCAGAGTGGAGGCTGAGGA
TCTGGGAGTTTATTACTGCTTTCAAGGTTCACATCTTCCGCTCACGTTCGGTGCTGGGACCAAGC
TGGAGCTGAAACGG

VLRendoMabA63 (protein)

\>VLRendoMabA63 (SEQ ID NO: 12)
DVLMTQTPLSLPVSLGDQASISCRSSQSIVYSNGKIYLEWYLQKPGQSPKLLIYKVSNRFSGVPDRFS
GSGSGTDFTLKISRVEAEDLGVYYCFQGSHLPLTFGAGTKLELKR In bold the CDRs according to the IMGT nomenclature

CDR1-IMGT-VLRA63
SQSIVYSNGKIYL (SEQ ID NO: 2)

CDR2-IMGT-VLRA63
KVS

CDR3-IMGT-VLRA63
FQGSHLPLT (SEQ ID NO: 4)

Sequence of the RA63 heavy chain

VHRendoMabA63 (nucleotide)

\>VHRendoMabA63 (SEQ ID NO: 13)
GAGGTGCAGCTTGTTGAGTCTGGTGGAGGATTGGTGCAGCCTAAAGGGTCATTGAAACTCTCAT
GTGCAGCCTCTGGATTCACCTTCAATATCTACGCCATGAACTGGATCCGCCAGGCTCCAGGAAA
GGGTTTGGAATGGATTGCTCGCATAAGAAGTAAAAGTAATAATTATGCAACATATTATGCCGATTC
AGTGAAAGACAGGTTCACCATCTCCAGAGATGATTCACAGAATATGGTCTATCTGCAAATGAACA
ACTTGAAAACTGAGGACACAGCCATGTATTACTGTGTGAGTTCCTATTACTCCGGTAGTTTCTTTG
CTTACTGGGGCCAAGGGACTCTGGTCACTGTCTCTGCA

VHRendoMabA63 (protein)

\>VHRendoMabA63 (SEQ ID NO: 14)
EVQLVESGGGLVQPKGSLKLSCAASGFTFNIYAMNWIRQAPGKGLEWIARIRSKSNNYATYYADSVK
DRFTISRDDSQNMVYLQMNNLKTEDTAMYYCVSSYYSGSFFAYWGQGTLVTSA In bold the CDRs according to the IMGT nomenclature

CDR1-IMGT-VHRA63
GFTFNIYA (SEQ ID NO: 6)

CDR2-IMGT-VHRA63
IRSKSNNYAT (SEQ ID NO: 8)

CDR3-IMGT-VHRA63
VSSYYSGSFFAY (SEQ ID NO: 10)

FIG.8

ANTIBODY AGAINST THE ENDOTHELIN RECEPTOR SUBTYPE A, AND USES THEREOF

SEQUENCE LISTING

The instant application contains a Sequence Listing which has been submitted electronically in ASCII format and is hereby incorporated by reference in its entirety. Said ASCII copy, created on Apr. 13, 2021, is named 531576US_SL.txt and is 9,362 bytes in size.

TECHNICAL FIELD

The present invention belongs to the technical field of antibodies, therapeutic and diagnostic use thereof and use thereof as a research tool.

More particularly, the present invention proposes an antibody, advantageously monoclonal, specific to the native and functional conformation of the endothelin receptor subtype A (ETA-R) and in particular human endothelin receptors expressed on the surface of the glial cells, such as glioma or glioblastoma cells.

The present invention also relates to the use of these antibodies for therapeutic and diagnostic purposes as well as for research purposes.

PRIOR ART

The receptors of the various endothelins (designated ET1, ET2 and ET3 in humans) belong to the family of receptors with seven transmembrane domains, also referred to as GPCRs, standing for "G Protein Coupled Receptors". Endothelin receptors have, in humans, two main subtypes, the subtype A (ETA-R) and the subtype B (ETB-R). The fact that these receptors are classified in the GPCR family confers on them a complex three-dimensional structure, closely linked to the membrane context in which they are situated.

Moreover, the conformational modification of GPCRs after fixing of the ligand thereof is widely described in the literature. The description of these conformational modifications associated with the bonding of the various intracellular proteins causing novel signalling cascades earned the Nobel prize in 2012 for Drs. Lefkowitz and Kobilka [1-3]. More recently, the work by Professors Doi and Nureki showed the conformational changes in the endothelin B receptor after fixing of the endothelin 1 ligand thereof [4].

The latter works are to be compared with the publications by the team of Professor Bagnato, which has shown the existence of an "endothelin axis" consisting of the type A receptor, the type B receptor, and the ligands thereof, the main one of which is endothelin 1 (ET-1) [5,6]. These works show that several tumour types (melanoma for the B receptor, glioblastoma for the A receptor) overexpress the endothelin A and/or B receptors and that these same tumour cells are capable of secreting ET-1 or capturing ET-1 secreted in the tumoral microenvironment by the endothelial cells that constitute the walls of the tumoral vessels feeding the tumours.

In other words, the tumour cells overexpressing the endothelin receptors are situated in a microenvironment rich in ET-1 that will then fix onto the endothelin A or B receptor, causing a change in conformation thereof in an "activated" configuration, overrepresented on the surface of these same tumour cells.

It should be noted that inventors have already produced antibodies making it possible to distinguish the various conformations of these receptors. The crystallographic work on the endothelin type B receptor described by Shihoya et al, 2016 [4] confirms the observations made on the melanoma cells with antibodies produced by the inventors [7,8].

Concerning the endothelin receptor subtype A, this also exhibits the same modification of its level of expression, particularly in colorectal cancer, in breast cancer, ovarian cancer, in glioblastomas (brain tumours) and in case of bladder cancer [9].

In addition, the endothelin axis and its receptors are also involved in several physiopathological functions and malfunctions. By way of non-limitative examples, mention can be made of arterial hypertension, atherosclerosis, coronary illnesses, renal malfunctioning, cerebrovascular diseases, Crohn's disease, pulmonary fibrosis, asthma, etc. (see the review by Shah, 2007 [10]).

Thus, targeting endothelin receptors and more particularly endothelin receptor subtype A therefore appears particularly relevant in human clinical biology [6,11].

Various strategies exist for blocking receptors, in particular for therapeutic purposes such as the use of antagonists, peptidic or not, and the use of monoclonal antibodies targeting these receptors.

However, in the passive immunotherapy arsenal for cancers using monoclonal antibodies (more than around sixty antibodies have been approved at the present time), none targets GPCRs. This is because the difficulty in obtaining specific monoclonal GPCR antibodies is a consequence of the problems related to the obtaining of these same receptors, in a native and functional form, outside the membrane context thereof.

Kondoh et al, 1990 [12] describes the bonding properties of four monoclonal antibodies (A2, G9, E7 and G10) against solubilised complexes of endothelin receptors present on the surface of rat pulmonary membranes. The G9 and G10 antibodies are immunoglobulins of type G and isotype 2a (IgG2a), whereas the A2 and E7 antibodies are IgG1 immunoglobulins. Though these four antibodies are indeed specific to solubilised endothelin receptors, Kondoh et al, 1990 [12] does not provide any information as to the fine specificities of these antibodies (ETA-R and/or ETB-R), with regard to the recognition of receptors of human origin, nor with regard to their properties.

The patent application CA 2 971 491 [13] describes twelve specific antibodies of the human endothelin receptor subtype A, designated A-1 to A-12. These antibodies have antagonist properties and are able to inhibit the signalling channel involving ET1. For this reason, the patent application CA 2 971 491 envisages using these antibodies in the treatment of pulmonary arterial hypertension.

The inventors therefore set out to obtain an antibody able to target particular conformers of the endothelin receptor subtype A expressed on the surface of cancer cells and in particular on the surface of human cancer cells.

DISCLOSURE OF THE INVENTION

The present invention makes it possible to solve the technical problems as defined above and to achieve the aim set out by the inventors.

Indeed the inventors have developed and used a particular immunisation and selection strategy already published to prepare specific antibodies of the endothelin receptor subtype B (International applications WO 2012/045776 [14] and WO 2017/220739 [15]). This strategy, coupled with a procedure for screening hybridomas in ELISA-cell and then by flow cytometry privileges the obtaining of specific monoclonal antibodies of endothelin receptors in the native conformative thereof. This approach furthermore has the advantage of not needing an extracted and purified receptor of interest, which still at the present time constitutes a challenge that is difficult to accommodate.

Through this strategy, the inventors have been able to select a monoclonal antibody directly against the endothelin receptor subtype A and in particular of the human subtype A, hereinafter referred to as Rendomab-A63 or RA63. This antibody does not have an antagonist character with regard to the pharmacological properties of endothelin receptor subtype A (ETA-R). In other words, the antibody according to the present invention is not capable of reducing, inhibiting or blocking one (or more) biological activities of ETA-R. On the other hand, the antibody according to the present invention is capable of recognising the particular conformers of endothelin receptor subtype A expressed on the surface of cancerous cells and in particular glioblastoma cells.

The present invention relates to an antibody directed against the endothelin receptor subtype A, or a fragment or derivative thereof.

Before going into any more detail in the description of the invention, we state or propose the following definitions.

The terms "antibody" and "immunoglobulin" are equivalent and can be used interchangeably in the present invention.

An antibody is a glycoprotein comprising at least two heavy chains (H) and at least two light chains (L) connected together by one or more disulfide bridges. Each heavy chain comprises a variable region (or domain) (VH) and a constant region comprising three domains, normally referred as CH1, CH2 and CH3. Each light chain comprises a variable region (or domain) (VL) and a constant region comprising a single domain, normally referred to as CL. The variable regions of the heavy chains and of the light chains involved in the recognition of the antigen can further be subdivided into three hypervariable regions, also referred to as "complementarity determining regions" (CDRs), framed by four more preserved regions, also referred to as framework regions (FRs). The organisation of each heavy chain (or light chain) variable region is, from the N-terminal end to the C-terminal end, as follows: FR1, CDR1, FR2, CDR2, FR3, CDR3 and FR4. In the context of the present invention, the definition of the CDRs and FRs that was used is that of the IMGT (the International ImMunoGeneTics database). The calculations of the identity percentages of the CDR sequences mentioned and claimed hereinafter are therefore to be taken into account on the basis of this annotation.

In addition, the term "antibody" includes, in the context of the present invention, not only complete antibody molecules but also fragments and derivatives thereof.

"Antibody fragment" means, in the context of the present invention, both a monovalent fragment that has a single antigen-binding site and also a divalent fragment that has two antigen-combining sites. Thus a fragment according to the invention has at least one antigen-binding site. Among these fragments, mention can be made of the Fab, F(ab')$_2$ and Fv fragments, and other fragments that preserve the antigen-binding site (scFv and diabody). A Fab fragment is a monovalent fragment consisting of the light chain entirely and part of the heavy chain (Fd) comprising the VH and CH1 domains as previously defined. An F(ab')$_2$ fragment is a divalent fragment corresponding to the association of two Fab fragments connected by the disulfide bridges present at the hinge region of the immunoglobulins situated between the constant domains CH1 and CH2. An Fv fragment is a monovalent fragment consisting solely of the variable regions VL and VH of the light and heavy chains of an antibody. An scFv fragment is a monovalent polypeptide fragment, solely obtained by genetic engineering, corresponding to the variable domains connected by a peptide bond. A diabody is a recombinant divalent antibody molecular consisting of two scFv molecules in opposite orientations because of a peptide bond that is too short to allow the formation of an scFv. The fragments according to the invention also cover the fragments as previously mentioned, the half-life of which has been increased by chemical modification, in particular by incorporation in a liposome or by introducing a polyalkylene glycol such as a polyethylene glycol (PEG), this technique being called "PEGylation" and giving fragments such as Fab-PEG, F(ab')$_2$-PEG or Fv-PEG. By the recombinant method, it is also possible to generate single or fused fragments of the antibody according to the present invention, having properties of penetrability of solid tumours and of pharmacokinetics that are more efficient and better controlled. The antibody fragments useful in the context of the present invention may be natural or recombinant.

"Antibody derivative" means, in the context of the present invention, antibody fragments obtained by genetic engineering such as single-chain Fv (scFv) and single domain antibodies (dAb). The term also includes molecules of the antibody type that can be produced using phage display techniques or other random selection techniques for molecules which bind to the endothelin receptor subtype A or to specific regions of this subtype.

Thus the "antibody fragments" and "antibody derivatives" cover all the molecules that contain a structure, advantageously peptidic, that forms part of the recognition site (that is to say the part of the antibody which binds to or combines with the epitope or the antigen) of an antibody according to the present invention. In addition, the antibody fragments and derivatives according to the present invention are capable of recognising the particular conformers of the endothelin receptor subtype A expressed on the surface of cancerous cells and in particular glioblastoma cells.

The present invention relates to an antibody directed against the endothelin receptor subtype A having:

i) at least one light-chain variable region, wherein the amino acid sequence:
   of the CDR1$_L$ has at least 60% identity with the following amino acid sequence: SQSIVYSNGKIYL (SEQ ID NO: 2);
   of the CDR2$_L$ has at least 60% identity with the following amino acid sequence: KVS;
   of the CDR3$_L$ has at least 60% identity with the following amino acid sequence: FQGSHLPLT (SEQ ID NO: 4); and ii) at least one heavy-chain variable region wherein the amino acid sequence:
   of the CDR1$_H$ has at least 60% identity with the following amino acid sequence: GFTFNIYA (SEQ ID NO: 6);
   of the CDR2$_H$ has at least 60% identity with the following amino acid sequence: IRSKSNNYAT (SEQ ID NO: 8);
   of the CDR3$_H$ has at least 60% identity with the following amino acid sequence: VSSYYSGSFFAY (SEQ ID NO: 10);

a fragment of this antibody or a derivative of this antibody.

In the context of the present invention, the amino acid sequences are given in accordance with the 1-letter international code.

Among the antibodies described in the patent application CA 2 971 491 [13], the antibodies designated A-7, A-8 and A-9 have at least one light-chain variable region close in terms of amino acid sequence to the light-chain variable region of the antibody according to the invention, but the amino acid sequences of the heavy-chain variable region and in particular the amino acid sequences of the $CDR2_H$ and $CDR3_H$ of the A-7, A-8 and A-9 antibodies are very far from the amino acid sequence of the heavy-chain variable region of the antibody according to the invention.

The antibody according to the present invention has at least one light-chain variable region wherein the CDR1 (i.e. $CDR1_L$) has at least 60% identity, at least 65% identity, at least 70% identity, at least 75% identity, at least 80% identity, at least 85% identity, at least 90% identity, at least 95% identity, at least 98% identity with the following amino acid sequence: SQSIVYSNGKIYL (SEQ ID NO: 2).

The antibody according to the present invention has at least one light-chain variable region wherein the CDR2 (i.e. $CDR2_L$) has at least 60% identity, at least 65% identity, at least 70% identity, at least 75% identity, at least 80% identity, at least 85% identity, at least 90% identity, at least 95% identity, at least 98% identity with the following amino acid sequence: KVS.

The antibody according to the invention has at least one light-chain variable region wherein the CDR3 (i.e. $CDR3_L$) has at least 60% identity, at least 65% identity, at least 70% identity, at least 75% identity, at least 80% identity, at least 85% identity, at least 90% identity, at least 95% identity, at least 98% identity with the following amino acid sequence: FQGSHLPLT (SEQ ID NO: 4).

It should be noted that, in the antibody according to the present invention, the identity percentages of the various CDRs in the light-chain variable region are independent of one another. For example, the $CDR2_L$ may have at least 65% with the following amino acid sequence: KVS, whereas the $CDR3_L$ may have at least 70% identity with the following amino acid sequence: FQGSHLPLT (SEQ ID NO: 4). Thus all the combinations in terms of identity percentage for the three CDRs of the light-chain variable region are envisaged in the present invention.

By way of particular example, the antibody according to the present invention comprises at least one light-chain variable region wherein the amino acid sequence:
of the $CDR1_L$ is SQSIVYSNGKIYL (SEQ ID NO: 2);
of the $CDR2_L$ is KVS; and
of the $CDR3_L$ is FQGSHLPLT (SEQ ID NO: 4).

Typically, the antibody according to the present invention comprises at least one light-chain variable region wherein the amino acid sequence has at least 60% identity with the following sequence:

(SEQ ID NO: 12)
DVLMTQTPLSLPVSLGDQASISCRSSQSIVYSNGKIYLEWYLQKPGQSPKL

LIYKVSNRFSGVPDRFSGSGSGTDFTLKISRVEAEDLGVYYCFQGSHLPLT

FGAGTKLELKR.

In particular, the antibody according to the present invention may comprise at least one light-chain variable region wherein the amino acid sequence has at least has at least 65% identity, at least 70% identity, at least 75% identity, at least 80% identity, at least 85% identity, at least 90% identity, at least 95% identity, at least 98% identity with the sequence SEQ ID NO: 12.

More particularly, the antibody according to the present invention may comprise one light-chain variable region wherein the amino acid sequence corresponds to the sequence SEQ ID NO: 12.

The antibody according to the present invention has at least one heavy-chain variable region wherein the CDR1 (i.e. $CDR1_H$) has at least 60% identity, at least 65% identity, at least 70% identity, at least 75% identity, at least 80% identity, at least 85% identity, at least 90% identity, at least 95% identity, at least 98% identity with the following amino acid sequence: GFTFNIYA (SEQ ID NO: 6).

The antibody according to the present invention has at least one heavy-chain variable region wherein the CDR2 (i.e. $CDR2_H$) has at least 60% identity, at least 65% identity, at least 70% identity, at least 75% identity, at least 80% identity, at least 85% identity, at least 90% identity, at least 95% identity, at least 98% identity with the following amino acid sequence: IRSKSNNYAT (SEQ ID NO: 8).

The antibody according to the present invention has at least one heavy-chain variable region wherein the CDR3 (i.e. $CDR3_H$) has at least 60% identity, at least 65% identity, at least 70% identity, at least 75% identity, at least 80% identity, at least 85% identity, at least 90% identity, at least 95% identity, at least 98% identity with the following amino acid sequence: VSSYYSGSFFAY (SEQ ID NO: 10).

It should be noted that, in the antibody according to the present invention, the identity percentages of the various CDRs in the heavy-chain variable region are independent of one another. For example, the $CDR2_H$ may have at least 75% with the following amino acid sequence: IRSKSNNYAT (SEQ ID NO: 8), whereas the $CDR3_L$ may have at least 65% identity with the following amino acid sequence: VSSYYSGSFFAY (SEQ ID NO: 10). Thus all the combinations in terms of identity percentage for the three CDRs of the heavy-chain variable region are envisaged in the present invention.

By way of particular example, the antibody according to the present invention comprises at least one heavy-chain variable region wherein the amino acid sequence:
of the $CDR1_H$ is GFTFNIYA (SEQ ID NO: 6);
of the $CDR2_H$ is IRSKSNNYAT (SEQ ID NO: 8); and
of the $CDR3_H$ is VSSYYSGSFFAY (SEQ ID NO: 10).

Typically, the antibody according to the present invention comprises at least one heavy-chain variable region wherein the amino acid sequence has at least 60% identity with the following sequence:

(SEQ ID NO: 14)
EVQLVESGGGLVQPKGSLKLSCAASGFTFNIYAMNWIRQAPGKGLEWIARI

RSKSNNYATYYADSVKDRFTISRDDSQNMVYLQMNNLKTEDTAMYYCVSSY

YSGSFFAYWGQGTLVTVSA.

In particular, the antibody according to the present invention may comprise at least one heavy-chain variable region wherein the amino acid sequence has at least 65% identity, at least 70% identity, at least 75% identity, at least 80% identity, at least 85% identity, at least 90% identity, at least 95% identity, at least 98% identity with the sequence SEQ ID NO: 14.

More particularly, the antibody according to the present invention may comprise at least one heavy-chain variable region wherein the amino acid sequence corresponds to the sequence SEQ ID NO: 14.

Advantageously, the antibody according to the invention has at least one light-chain variable region and at least one heavy-chain variable region as defined previously.

Thus the antibody according to the invention has at least one light-chain variable region comprising a $CDR1_L$, a $CDR2_L$ and a $CDR3_L$ as previously defined and at least one heavy-chain variable region comprising a $CDR1_H$, a $CDR2_H$ and a $CDR3_H$ as previously defined.

The light chain of the antibody according to the invention is typically a kappa light chain.

The heavy chain of the antibody according to the invention is in particular a gamma 2b heavy chain.

In particular, the antibody according to the present invention is a type G immunoglobulin.

More particularly, the antibody according to the present invention is an immunoglobulin of type IgG2b/kappa.

The antibody directed against the endothelin receptor subtype A that is the object of the present invention selectively binds extracellular segments of the ETA-R. "Antibody that selectively binds" at least one specified domain or region of the ETA-R, in particular the human ETA-R, means, in the context of the present invention, an antibody that binds the specific domain or domains with a greater affinity than any other region of the ETA-R. Advantageously, the antibody binds the specified domain or domains of the ETA-R with an affinity at least 2, or at least 5, or at least 10, or at least 50 times greater than it has for any other region of the ETA-R. This binding can be determined by methods well known in the field, such as flow cytometry, radioimmunoassay (RIA), confocal microscopy, enzymatic immunoassay assay (EIA) by direct or indirect revelation of the antibody to be tested (ELISA).

The antibody that is the object of the present invention can be obtained from an animal immunised against the endothelin receptor subtype A or against a fragment of this receptor comprising the epitope or epitopes recognised by the antibody according to the present invention. The immunised animal may be any animal normally used for producing antibodies, such as a mouse, a rat, a rabbit, a goat, a dog, a horse or a camelid such as a camel or llama. The antibody that is the object of the present invention may also be obtained from a bank of antibodies or fragments of antibodies selected against the endothelin receptor subtype A or against a fragment of this receptor comprising the epitope or epitopes recognised by the antibody according to the present invention. The bank of antibodies or fragments of antibodies may be generated from any animal normally used for the production of antibodies such as a mouse, a rat, a rabbit, a goat, a dog, a horse or a camelid such as a camel or llama but also from a non-human primate or from a human.

The antibody thus obtained may be purified on an affinity column on which the endothelin receptor subtype A or one of the sequences specifically recognised by the antibody according to the invention has previously been immobilised. This purification may also involve protein A affinity chromatography.

In the context of the present invention, the antibody may be a polyspecific or monospecific polyclonal antibody, or a monoclonal antibody.

Advantageously, the antibody of the present invention is monoclonal. A "monoclonal antibody" refers, by standard definition in immunology, to an antibody obtained from a population of substantially homogeneous antibodies, i.e. a population of identical antibodies, a relatively small quantity thereof optionally being able to have a mutation. A monoclonal antibody is obtained from the proliferation of a single clone of cells such as a hybridoma.

More particularly, the antibody according to the present invention is the monoclonal murine antibody obtained from the hybridoma deposited at the CNCM (standing for "Collection Nationale de Cultures de Microorganismes", Institut Pasteur, 25 rue du Docteur Roux, 75724 PARIS Cedex 15) on 18 Oct. 2017 under the CNCM number 1-5250 (Rendomab-A63). The present invention also relates to such a hybridoma.

In a variant, the antibody according to the present invention may be a chimeric antibody, i.e. an antibody that contains heavy- and light-chain variable regions and hypervariable regions derived from an antibody of a given species in combination with heavy- and light-chain constant regions derived from an antibody of another species heterologous with the previous one.

A first variant of the present invention corresponds to a chimerised antibody and in particular a chimerised monoclonal antibody, that is to say an antibody wherein the variable domains issuing from the previously described murine antibody are associated with constant domains of human origin. It should be stated that several therapeutic antibodies in use in humans are chimerised antibodies.

A second particularly interesting variant may be a humanised antibody and in particular a humanised monoclonal antibody. This is because it is preferable to use a humanised antibody if this must be administered repeatedly to a human subject.

In the case of a humanised monoclonal antibody according to the present invention, this may be prepared by inserting CDRs of a murine antibody and in particular of the murine antibody issuing from the hybridoma deposited at the CNCM on 18 Oct. 2017 under the number CNCM I-5250 in a human antibody, whatever the isotype thereof (IgG, IgA, IgM). Humanised antibodies may be prepared using the techniques and approaches described in Verhoeyen et al, 1988 [16] and in the U.S. Pat. No. 4,816,567 [17].

The antibodies may also be human antibodies in that they have the sequence of amino acids of anti-ETA-R human antibodies via preparation methods known in the field that do not require the vaccination of humans. For example, such antibodies may be obtained by gene immunisation/cell immunisation boosters of transgenic mice that are available and by essence contain human immunoglobulin genes (see Vaughan et al, 1998 [18]). In a variant, such antibodies may be obtained by cloning coding cDNA from human B lymphocytes directed against ETA-R.

The present invention also relates to an isolated polynucleotide chosen from the following various polynucleotides:

α) a polynucleotide coding an antibody as previously defined;

β) a polynucleotide that is complementary to the polynucleotide as defined at point (α);

γ) a polynucleotide of at least 18 nucleotides, capable of hybridising under high-stringency conditions to the polynucleotides as defined at points (α) and (β).

"Polynucleotide", in the context of the present invention, means a nucleic acid, a nucleic sequence, a nucleic acid sequence, an oligonucleotide, a polynucleotide sequence, a nucleotide sequence, a single-strand DNA, a double-strand DNA or an RNA. A polynucleotide according to the present invention may comprise natural nucleotides and non-natural nucleotides.

The polynucleotide according to the invention does not correspond to a nucleotide sequence in its natural state, i.e. in its natural chromosome environment. On the contrary, the polynucleotide according to the invention has been isolated and optionally purified, and the environment thereof has consequently been modified. The polynucleotide according to the invention may also be obtained by genetic recombination or by chemical synthesis.

High-stringency conditions correspond to conditions of temperature and ionic force that make it possible to obtain a hybridisation between two complementary nucleotide sequences. A person skilled in the art will be able to determine the high-stringency conditions best suited in particular according to the size of the nucleotide sequences, and this with reference to the teaching of Sambrook et al, 1989 [19].

The polynucleotide according to the present invention comprises:

i') at least one nucleotide sequence coding a light-chain variable region and comprising:
- a $1^{st}$ sequence coding $CDR1_L$ and having at least 60% identity with the following nucleotide sequence: AGT CAG AGC ATT GTA TAT AGT AAT GGA AAA ATC TAT TTA (SEQ ID NO: 1);
- a $2^{nd}$ sequence coding $CDR2_L$ and having at least 60% identity with the following nucleotide sequence: AAA GTT TCC;
- a $3^{rd}$ sequence coding $CDR3_L$ and having at least 60% identity with the following nucleotide sequence: TTT CAA GGT TCA CAT CTT CCG CTC ACG (SEQ ID NO: 3); and ii') at least one nucleotide sequence coding a heavy-chain variable region and comprising:
- a $1^{st}$ sequence coding $CDR1_H$ and having at least 60% identity with the following nucleotide sequence: GGA TTC ACC TTC AAT ATC TAC GCC (SEQ ID NO: 5);
- a $2^{nd}$ sequence coding $CDR2_H$ and having at least 60% identity with the following nucleotide sequence: ATA AGA AGT AAA AGT AAT AAT TAT GCA ACA (SEQ ID NO: 7);
- a $3^{rd}$ sequence coding $CDR3_H$ and having at least 60% identity with the following nucleotide sequence: GTG AGT TCC TAT TAC TCC GGT AGT TTC TTT GCT TAC (SEQ ID NO: 9).

The polynucleotide according to the present invention has at least one nucleotide sequence coding a light-chain variable region and having a $1^{st}$ sequence coding $CDR1_L$, said $1^{st}$ sequence having at least 60% identity, at least 65% identity, at least 70% identity, at least 75% identity, at least 80% identity, at least 85% identity, at least 90% identity, at least 95% identity, at least 98% identity with the following nucleotide sequence: AGT CAG AGC ATT GTA TAT AGT AAT GGA AAA ATC TAT TTA (SEQ ID NO: 1).

The polynucleotide according to the present invention has at least one nucleotide sequence coding a light-chain variable region and having a $2^{nd}$ sequence coding $CDR2_L$, said $2^{nd}$ sequence having at least 60% identity, at least 65% identity, at least 70% identity, at least 75% identity, at least 80% identity, at least 85% identity, at least 90% identity, at least 95% identity, at least 98% identity with the following nucleotide sequence: AAA GTT TCC.

The polynucleotide according to the present invention has at least one nucleotide sequence coding a light-chain variable region and having a $3^{rd}$ sequence coding $CDR3_L$, said $3^{rd}$ sequence having at least 60% identity, at least 65% identity, at least 70% identity, at least 75% identity, at least 80% identity, at least 85% identity, at least 90% identity, at least 95% identity, at least 98% identity with the following nucleotide sequence: TTT CAA GGT TCA CAT CTT CCG CTC ACG (SEQ ID NO: 3).

It should be noted that, in the polynucleotide according to the present invention, the identity percentages of the sequences coding the various CDRs in a light-chain variable region are independent of one another. For example, the sequence coding $CDR2_L$ may have at least 65% with the following nucleotide sequence: AAA GTT TCC, whereas the sequence coding $CDR3_L$ may have at least 70% identity with the nucleotide sequence (SEQ ID NO: 3). Thus all the combinations in terms of identity percentage for the three sequences coding the various CDRs of the light-chain variable region are envisaged in the present invention.

By way of particular example, the polynucleotide according to the present invention comprises at least one nucleotide sequence coding a light-chain variable region and comprising:

a $1^{st}$ sequence coding $CDR1_L$ the nucleotide sequence of which is:

(SEQ ID NO: 1)
AGT CAG AGC ATT GTA TAT AGT AAT GGA AAA ATC TAT TTA;

a $2^{nd}$ sequence coding $CDR2_L$ the nucleotide sequence of which is:

AAA GTT TCC;

a $3^{rd}$ sequence coding $CDR3_L$ the nucleotide sequence of which is:

(SEQ ID NO: 3)
TTT CAA GGT TCA CAT CTT CCG CTC ACG.

It is clear that the above three sequences listed (i.e. SEQ ID NO: 1, AAA GTT TCC and SEQ ID NO: 3) must be organised with respect to one another so that the polypeptide obtained following the translation of the polynucleotide according to the invention comprises three peptide sequences having at least 60% identity and advantageously 100% identity with the $CDR1_L$, $CDR2_L$ and $CDR3_L$ of the light-chain variable region as previously defined.

Typically, the polynucleotide according to the present invention comprises at least one nucleotide sequence coding a light-chain variable region the nucleotide sequence of which has at least 60% identity with the following sequence:

(SEQ ID NO: 11)
GAT GTT TTG ATG ACC CAA ACT CCA CTC TCC CTG CCT GTC

AGT CTT GGA GAT CAA GCC TCC ATC TCG TGC AGA TCT AGT

CAG AGC ATT GTA TAT AGT AAT GGA AAA ATC TAT TTA GAA

TGG TAC CTG CAG AAA CCA GGC CAG TCT CCA AAG CTC CTA

ATC TAC AAA GTT TCC AAC CGA TTT TCT GGG GTC CCA GAC

AGG TTC AGT GGC AGT GGA TCA GGG ACA GAT TTC ACA CTC

AAG ATC AGC AGA GTG GAG GCT GAG GAT CTG GGA GTT TAT

TAC TGC TTT CAA GGT TCA CAT CTT CCG CTC ACG TTC GGT

GCT GGG ACC AAG CTG GAG CTG AAA CGG.

In particular, the polynucleotide according to present invention comprises at least one nucleotide sequence coding a light-chain variable the nucleotide sequence of which has at least 65% identity, at least 70% identity, at least 75% identity, at least 80% identity, at least 85% identity, at least 90% identity, at least 95% identity, at least 98% identity with the sequence: SEQ ID NO: 11.

More particularly, the polynucleotide according to the present invention comprises at least one nucleotide sequence coding a light-chain variable region the nucleotide sequence of which corresponds to the sequence SEQ ID NO: 11.

The polynucleotide according to the present invention also has at least one nucleotide sequence coding a heavy-chain variable region and having a $1^{st}$ sequence coding $CDR1_H$, said $1^{st}$ sequence having at least 60% identity, at least 65% identity, at least 70% identity, at least 75% identity, at least 80% identity, at least 85% identity, at least 90% identity, at least 95% identity, at least 98% identity with the following nucleotide sequence: GGA TTC ACC TTC AAT ATC TAC GCC (SEQ ID NO: 5).

The polynucleotide according to the present invention has at least one nucleotide sequence coding a heavy-chain variable region and having a $2^{nd}$ sequence coding $CDR2_H$, said $2^{nd}$ sequence have at least 60% identity, at least 65% identity, at least 70% identity, at least 75% identity, at least 80% identity, at least 85% identity, at least 90% identity, at least 95% identity, at least 98% identity with the following nucleotide sequence: ATA AGA AGT AAA AGT AAT AAT TAT GCA ACA (SEQ ID NO: 7).

The polynucleotide according to the present invention has at least one nucleotide sequence coding a heavy-chain variable region having a $3^{rd}$ sequence coding $CDR3_H$, said $3^{rd}$ sequence having at least 60% identity, at least 65% identity, at least 70% identity, at least 75% identity, at least 80% identity, at least 85% identity, at least 90% identity, at least 95% identity, at least 98% identity with the following nucleotide sequence: GTG AGT TCC TAT TAC TCC GGT AGT TTC TTT GCT TAC (SEQ ID NO: 9).

It should be noted that, in the polynucleotide according to the present invention, the identity percentages of the sequences coding the various CDRs in a heavy-chain variable region are independent of one another. For example, the sequence coding $CDR2_H$ may have at least 75% with the nucleotide sequence SEQ ID NO: 7, whereas the sequence coding $CDR3_H$ may have at least 65% identity with the nucleotide sequence (SEQ ID NO: 9). Thus all the combinations in terms of identity percentage for the three sequences coding the various CDRs of the heavy-chain variable region are envisaged in the present invention.

By way of particular example, the polynucleotide according to the present invention comprises at least one nucleotide sequence coding a heavy-chain variable region and comprising:

a $1^{st}$ sequence coding $CDR1_H$ the nucleotide sequence of which is:

(SEQ ID NO: 5)
GGA TTC ACC TTC AAT ATC TAC GCC;

a $2^{nd}$ sequence coding $CDR2_H$ the nucleotide sequence of which is:

(SEQ ID NO: 7)
ATA AGA AGT AAA AGT AAT AAT TAT GCA ACA;

a $3^{rd}$ sequence coding $CDR3_L$ the nucleotide sequence of which is:

(SEQ ID NO: 9)
GTG AGT TCC TAT TAC TCC GGT AGT TTC TTT GCT TAC.

It is clear that the three sequences listed above (i.e. SEQ ID NO: 5, SEQ ID NO: 7 and SEQ ID NO: 9) must be organised with respect to one another so that the polypeptide obtained following the translation of the polynucleotide according to the invention comprises three peptide sequences having at least 60% identity and advantageously 100% identity with $CDR1_H$, $CDR2_H$ and $CDR3_H$ of the heavy-chain variable region as previously defined.

Typically, the polynucleotide according to the present invention comprises at least one nucleotide sequence coding a heavy-chain variable region the nucleotide sequence of which has at least 60% identity with the following sequence:

(SEQ ID NO: 13)
GAG GTG CAG CTT GTT GAG TCT GGT GGA GGA TTG GTG CAG

CCT AAA GGG TCA TTG AAA CTC TCA TGT GCA GCC TCT GGA

TTC ACC TTC AAT ATC TAC GCC ATG AAC TGG ATC CGC CAG

GCT CCA GGA AAG GGT TTG GAA TGG ATT GCT CGC ATA AGA

AGT AAA AGT AAT AAT TAT GCA ACA TAT TAT GCC GAT TCA

GTG AAA GAC AGG TTC ACC ATC TCC AGA GAT GAT TCA CAG

AAT ATG GTC TAT CTG CAA ATG AAC AAC TTG AAA ACT GAG

GAC ACA GCC ATG TAT TAC TGT GTG AGT TCC TAT TAC TCC

GGT AGT TTC TTT GCT TAC TGG GGC CAA GGG ACT CTG

GTC ACT GTC TCT GCA.

In particular, the polynucleotide according to the present invention comprises at least one nucleotide sequence coding a heavy-chain variable region the nucleotide sequence of which has at least 65% identity, at least 70% identity, at least 75% identity, at least 80% identity, at least 85% identity, at least 90% identity, at least 95% identity, at least 98% identity with the sequence SEQ ID NO: 13.

More particularly, the polynucleotide according to the present invention comprises at least one nucleotide sequence coding a heavy-chain variable region the nucleotide sequence of which corresponds to the sequence SEQ ID NO: 13.

"Identity percentage" between two amino acid sequences (or between two nucleotide sequences) means, in the context of the present invention, a percentage of amino acid residues (or of nucleotides) that are identical between the two sequences compared, this percentage being obtained after implementation of the best alignment (optimum alignment) between the two sequences. A person skilled in the art know various techniques for obtaining such identity percentage involving homology algorithms or computer programs such as the BLAST program.

The identity percentage is statistical and the differences between the two sequences are distributed randomly along these sequences. The differences between the two sequences may consist of various types of modifications of the sequences: deletions, substitutions or additions of residues of amino acids (or of nucleotides).

In a $1^{st}$ embodiment, the modifications made in the sequences result in substitutions between equivalent amino acids i.e. amino acids having structural homologies or not substantially modifying the biological activity of the corresponding antibodies.

In a $2^{nd}$ embodiment, the modifications made in the sequences result in substitutions by non-equivalent amino acids i.e. amino acids not having structural homology. These modifications are able to improve the biological properties of the antibody i.e. improved affinity and/or specificity, broadened recognition spectrum, increase in stability, reduction in immunogenicity, etc.

Prior to the two embodiments disclosed previously, these modifications, insertions or deletions may target a CDR essential or not to the properties of the antibody according to the invention.

Applied to the two embodiments disclosed above, these modifications, insertions or deletions may also target an FR region, knowing that such regions, in variable domains of the antibodies, may, depending on the antibodies, also play a role in the expression of the properties of the antibody according to the invention.

The present invention also relates to a cloning and/or expression vector containing at least one polynucleotide according to the present invention. Such a vector is in particular useful for transforming a host organism and expressing therein an antibody according to the present invention.

The vector according to the present invention further comprises one (or more) elements that allow expression of the polynucleotide according to the present invention and/or the secretion of the product resulting from the translation of the polynucleotide according to the present invention. Among these elements, mention can be made of a constitutive or inducible promoter, a signal initiating the transcription or a signal terminating the transcription, a sequence initiating the translation or an end-of-translation signal.

Advantageously, the vector according to the present invention comprises a promoter, a polynucleotide of the invention and a terminator element which are operationally linked to each other. "Operationally linked to each other" means, according to the invention, elements linked to each other so that the functioning of one of the elements is affected by that of another one. By way of example, a promoter is operationally linked to a coding sequence when it is capable of affecting the expression thereof. The elements regulating the transcription, the translation and the maturation of the peptides that the vector may comprise are known to a person skilled in the art and the latter is capable of choosing according to the host organism in which the expression or cloning must be performed.

The vector according to the present invention is advantageously chosen from a plasmid, a cosmid, a bacteriophage and a virus such as a baculovirus. In particular, the vector of the invention is an autonomously replicating vector including elements enabling it to be maintained and replicated in the host organism as a replication origin. Furthermore, the vector may include elements enabling it to be selected, in the host organism such as for example an antibiotic resistance gene or a selection gene that ensures complementation with the respective gene deleted in the genome of the host organism. Such cloning and/or expression vectors are well known to persons skilled in the art and widely described in the literature.

The invention also relates to a host organism transformed by or comprising a polynucleotide according to the present invention or a vector according to the present invention.

"Host organism" means any isolated, uni- or pluricellular, lower or higher organism, wherein a polynucleotide of the invention is introduced in order to produce an antibody according to the present invention.

A person skilled in the art knows various methods for effectively introducing a polynucleotide into a host organism, so that, in the host organism, the antibody coded by said polynucleotide is produced. By way of example and non-exhaustively, this method may be an electroporation, a lipofection, a biological transformation of a plant using *Agrobacterium* tumefasciens, a thermal shock or a chemical method.

Advantageously, the host organism is a microorganism such as a yeast, a bacterium or a fungus. Transforming such microorganisms makes it possible to produce the antibody of the invention on a semi-industrial or industrial scale.

In a variant, the host organism is an animal cell such as mammal cell, a plant cell, an insect cell, an animal with the exception of a human, or a plant.

Such host organisms can be used to produce an antibody according to the present invention. A method for producing an antibody according to the present invention comprises the steps of:

a) culturing a host organism according to the present invention and in particular a single-cell host organism in a culture medium and under suitable conditions;

b) recovering said antibody from the culture medium of said cultured host organism or from said cultured host organism.

The antibody according to the present invention can also be modified in order to a) generate an antibody marked by a radioactive isotope, a prodrug, an enzyme or a toxin, and b) modify the binding specificity and/or affinity, and/or the stability and/or the immunogenicity of said antibody ensuring the targeting of the cells that overexpress ETA-R, in particular cancerous cells such as glioblastomas, etc.

The antibody according to the present invention can also be modified in order to couple it chemically or genetically to a peptide molecule; a protein molecule; a nucleic molecule such as a DNA, an RNA, an RNAi, an aptamer, a PNA or a LNA; a lipid molecule; a carbohydrate molecule or a chemical molecule.

The present invention therefore relates to a compound comprising an antibody according to the present invention conjugated with an element chosen from the group consisting of a cytotoxic group, an easily detectable group or an effector group.

"Cytotoxic group" means a group directly or indirectly toxic for the cells targeted by the antibody according to the present invention. "Directly cytotoxic" means a group that is in itself cytotoxic. "Indirectly cytotoxic" means a group which, although not cytotoxic in itself, may cause cytotoxicity, for example through its action on another molecule or through a supplementary action on it.

In a $1^{st}$ embodiment, the cytotoxic group is a cytotoxic chemotherapy agent. A person skilled in the art knows various cytotoxic chemotherapy agents that can be used in the context of the present invention. The activity of these agents can be increased under irradiation. By way of illustrative and non-limitative examples, mention can be made of alkylating agents such as mechlorethamine or chlorambucil; methotrexate; 5-fluoro-uracil; vinblastine; gemcitabine; fludarabine; nicotinamide; doxorubicin; mitomycin; L-asparaginase; cisplatin; taxol and analogues/derivatives thereof.

In a $2^{nd}$ embodiment, the cytotoxic group is a cytotoxic (poly)peptide group such as ricin, abrin, *Pseudomonas* exotoxin, TNFα and interleukin 2.

In a $3^{rd}$ embodiment, the cytotoxic group is an indirectly cytotoxic chemotherapy agent. Such agent, also referred to as a prodrug, is not cytotoxic or only slightly cytotoxic as such but is able to give, in particular following an enzymatic reaction or an irradiation, a cytotoxic substance (or drug) in particular as defined in the $1^{st}$ embodiment. By way of illustrative and non-limitative examples, mention can be made of methotrexate-alanine; mitomycin phosphate, 5-fluorocytosine, photofrin and capecitabine.

In a $4^{th}$ embodiment, the cytotoxic group is an indirectly cytotoxic (poly)peptide group. Indirectly cytotoxic (poly) peptide group means a (poly)peptide that has an enzyme activity and can convert a relatively non-toxic prodrug in particular as defined in the $3^{rd}$ embodiment into a cytotoxic substance in particular as defined in the $1^{st}$ embodiment. Among such indirectly cytotoxic (poly)peptide groups mention can be made of a peptidase such as a carboxypeptidase, an aminopeptidase or an endopeptidase; a phosphatase; a sulfatase; an amidase; a kinase; a glycosidase; a deaminase; a reductase and an oxidase.

In a $5^{th}$ embodiment, the cytotoxic group is a nucleic acid molecule that is directly or indirectly cytotoxic, such as an antisense oligonucleotide or an aptamer.

In a $6^{th}$ embodiment, the cytotoxic group is a radioactive isotope such as iodine-131, yttrium-90, lutetium-177, copper-67 or lead-212.

A person skilled in the art knows various techniques for conjugating groups with an antibody according to the present invention once the latter is obtained or produced.

These techniques allow covalent coupling between an antibody according to the invention and a cytotoxic group, taking advantage of the particular chemical groups carried by the antibody according to the invention and by the cytotoxic group. Among these particular chemical groups, mention can be made of a thiol group, an ester group, an amino group, an acid group and any chemical element able to be used in click chemistry.

In a variant and in particular when the cytotoxic group is a group of a peptide nature, this conjugation may consist of producing the compound according to the invention in the form of a fusion compound by genetic recombination techniques, wherein a polynucleotide comprises respective regions coding the antibody according to the present invention and the cytotoxic group, adjacent to each other, juxtaposed or separated by a region coding a peptide linker that does not destroy the required properties of the final hybrid compound.

Whatever the technique used for conjugating an antibody of the present invention with a cytotoxic group, the only constraint to be complied with in the context of this conjugation is that the conjugated antibody keeps its binding specificity for ETA-R, a property associated with those of the cytotoxic group.

"Easily detectable group" means, in the context of the present invention, a group that can be detected using an advantageously non-invasive suitable detection technique such as microscopy, scintigraphy and magnetic resonance imaging (MRI). A compound according to the invention comprising such an easily detectable group is suitable for the field of imaging and diagnostics. It makes it possible in particular to identify and locate sites at which ETA-R is overexpressed because of the binding specificity to ETA-R of the antibody present in this compound.

In a $1^{st}$ embodiment, the easily detectable group may be an enzyme or a molecule capable of generating a detectable and possibly quantifiable signal under particular conditions such as the presence of a suitable substrate. By way of illustrative and non-limitative examples, mention can be made of biotin, digoxygenin, 5-bromodeoxyuridine, an alkaline phosphatase, a peroxidase, an acetylcholine esterase (AChE), a glucose amylase and a lysozyme.

In a $2^{nd}$ embodiment, the easily detectable group may be a fluorescent, chemifluorescent or bioluminescent marker such as fluorescein and derivatives thereof; rhodamine and derivatives thereof; GFP (standing for "Green Fluorescent Protein") and derivatives thereof; umbelliferone and derivatives thereof; luminol; luciferase and luciferin.

In a $3^{rd}$ embodiment, the easily detectable group may be a radioactive label or isotope such as iodine-123, iodine-125, iodine-126, iodine-133, indium-111, indium-113m, bromine-77, gallium-67, gallium-68, ruthenium-95, ruthenium-97, technetium-99m, fluorine-18, carbon-13, nitrogen-15, oxygen-17, scandium-47, tellurium-122m, thulium-165 and yttrium-199. It should be noted that some radioactive atoms used as easily detectable groups may also constitute cytotoxic groups because of the quantity of radioactivity that they are able to deliver.

Everything explained above with regard to the conjugation of the antibody according to the invention with cytotoxic groups applies mutatis mutandis to the conjugation of the antibody according to the invention with easily detectable groups. The conjugation of the antibody according to the invention with the easily detectable groups can also be achieved in relation to nano-objects, in order to densify the concentration thereof, and therefore to improve the emitted signal, the contrast or the toxicity.

In the case where this easily detectable group is a radioactive label, it may be introduced into the peptide sequence of the antibody according to the invention. This introduction may take place during the synthesis of the antibody using one or more marked amino acids. In a variant, this introduction may take place following this synthesis by fixing the radioactive label on residues of the peptide sequence of the synthesised antibody. For example, yttrium-90 may be fixed via a lysin residue. In a variant also, the radioactive label may be directly fixed to the antibody by known means. For example, EDTA or another chelating agent may be bound to the antibody according to the invention and used to bind indium-111.

The present invention relates to the use of a compound comprising an antibody and an easily detectable group as a diagnostic, prognostic and in vivo monitoring tool which is very efficient in medical imaging. The antibody format is chosen so as to generate the best signal-to-noise ratio and the best pharmacokinetics.

In other words, the present invention relates to a method for detecting and quantifying in vivo or in vitro the expression or overexpression of the endothelin receptor subtype A, comprising:

$a_1$) putting a biological sample in contact with a compound according to the present invention;

$b_1$) detecting any complex between said compound and said endothelin receptor subtype A.

Such a method can be used for detecting, diagnosing, prognosticating or monitoring a state in which the endothelin receptor subtype A is overexpressed and in particular for detecting, diagnosing, prognosticating or monitoring a cancer state (presence, size and development of cancer tumours). In the case of a method for diagnosing a cancer such as a glioblastoma, this comprises the steps of:

$a_1'$) putting a biological sample of the subject in contact with a compound according to the present invention;

$b_1'$) detecting the signal emitted by the easily detectable group, and $c_1'$) determining the presence or absence of a cancer in said subject on the basis of the signal detected at step ($b_1'$) optionally compared with a control signal.

"Control signal" means, in the context of the present invention, a signal or a mean signal value obtained for a healthy subject or, on the other hand, a signal or a mean signal value obtained for a cancer subject.

In a particular embodiment, the diagnostic method according to the invention is a method performed in vitro for which the biological sample such as a biopsy has been taken from the subject before implementing step ($a_1'$). In a variant, this method may correspond to an in vivo imaging method in which an effective quantity of the compound according to the invention has previously been administered to the subject. "Effective quantity" means a quantity of compound sufficient for imaging cancers. This quantity varies according to the administration mode, the formulation administered, the excipient, and the cancer to be diagnosed. However, determining this effective quantity is routine work for a person skilled in the art.

"Effector group" means, in the context of the present invention, a group capable of specifically recognising a cancer marker, or which allows the recruitment (i) of an effector cell of the immune system, i.e. NK cells, cytotoxic T cells or macrophages, or (ii) of the system of the complement. "Group capable of specifically recognising a cancer marker" means, in the context of the present invention, a ligand of a cancer marker; an antibody identical to or different from an antibody according to the present invention; a protein; a peptide; or a nucleic molecule such as a DNA, an RNA, an RNAi, an aptamer, a PNA or an LNA. By "cancerous marker", both an ETA-R and another membrane marker is envisaged.

In a $1^{st}$ embodiment, the effector group recognises a cancer marker, identical to or different from ETA-R, expressed on the surface of cancer cells, providing better recognition specificity and therefore increased targeting of cancerous cells.

In a $2^{nd}$ embodiment, the effector group has a recognition specificity for a marker specifically present on the surface of effector cells of the immune system, i.e. NK or macrophage cells or cytotoxic T cells. Such a recruitment provides the targeted lysis of the cancerous cells recognised by the antibody of the present invention.

In a $3^{rd}$ embodiment, the effector group has a recognition specificity for the system of the complement and, in particular, for the C1 protein or the truncated form C1q thereof, which initiates the cascade of the molecular events that result in the death of the targeted cell. Such a recruitment provides the targeted lysis of the cancer cells recognised by the antibody of the present invention.

In a $4^{th}$ embodiment, the effector group has a recognition specificity for the system of the complement and, in particular, for the C3 protein and the truncated form C3b thereof, thus providing the recruitment of effector cells of the immune system, cells that cause the death of the targeted cell. Such recruitment provides the targeted lysis of the cancer cells recognised by the antibody of the present invention.

The present invention relates to an antibody according to the present invention, a polynucleotide according to the present invention or a compound according to the present invention for use as a drug.

Thus the present invention relates to a pharmaceutical composition comprising, as active principle, an antibody according to the present invention, or a polynucleotide according to the present invention, or a compound according to the present invention, and a pharmaceutically acceptable vehicle.

"Pharmaceutically acceptable vehicle" means, according to the present invention, a substance that is added to an antibody, a polynucleotide, or a compound according to the present invention for favouring transport thereof, preventing substantial degradation thereof in said composition and/or increasing the half-life thereof. Advantageously, such a pharmaceutically acceptable vehicle is sterile and apyrogenic. It is chosen according to the type of application of the pharmaceutical composition of the invention and in particular according to the administration method thereof.

Thus the pharmaceutical composition according to the invention consists of at least one antibody, or a polynucleotide or a compound according to the present invention in free form or in the form of an addition salt with a pharmaceutically acceptable acid, in the pure state or in the form of a composition in which it is associated with any other pharmaceutically compatible product. The pharmaceutical compositions according to the invention can be employed systemically; by parenteral route, for example by intravenous, intra-arterial, intraperitoneal, intrathecal, intraventricular, intrasternal, intracranial, intramuscular or subcutaneous route; topically; orally; rectally; intranasally or by inhalation.

As solid compositions for oral administration, use can be made of tablets, pills, powders, etc. in which the antibody, the polynucleotide or the compound according to the invention are mixed with one or more inert diluents conventionally used, and optionally with other substances such as for example a lubricant, a dye, a coating, etc.

As liquid compositions for oral or ocular administration use can be made of pharmaceutical acceptable suspensions, solutions, emulsions or syrups containing inert diluting agents conventionally used, and optionally other substances such as wetting agents, sweeteners, thickeners, etc.

The sterile compositions for parenteral administration may be aqueous or non aqueous solutions, suspensions or emulsions. As solvent or vehicle, use can be made of water, propylene glycol, plant oils or other suitable organic solvents. These composition may also contain adjuvants, such as wetting agents, isotonisers, emulsifiers, etc.

The compositions for topical administration may for example be creams, lotions, throat sprays, nasal or eye drops or aerosol.

The daily dose of the antibody, of the polynucleotide or of the compound according to the present invention is normally from 1 to 1000 mg per adult (that is to say approximately 0.015 to 15 mg/kg), administered in single or fractionated doses. These doses are given only by way of illustration. The physician, in all cases, will be able to determine the actual dose most suited to a given individual patient, and this varies according to the age, weight and response of the patient.

The present invention relates to an antibody according to the present invention, a polynucleotide according to the present invention, a compound according to the present invention or a pharmaceutical composition according to the present invention for use in the treatment and/or prevention of an illness or a pathology involving a malfunction, direct or in association with another physiological route, of the axis comprising an endothelin and at least one of the receptors thereof such as in particular the endothelin receptors subtype A.

Advantageously, such an illness or pathology is a cancer. As cancers, mention can be made of a melanoma, colorectal cancer, colon cancer, Kaposi's sarcoma, a glioblastoma, ovarian cancer and bladder cancer. Typically, this illness is a glioblastoma.

In other words again, the present invention relates to a method for treatment and/or preventing an illness or pathology involving malfunctioning, direct or in association with another physiological route, of the axis comprising endothelin and at least one of the receptors thereof such as particular endothelin receptor subtype A in a patient suffering from or liable to suffer from such an illness or pathology. This method comprises administering to said patient an effective quantity of an antibody according to the present invention, of a polynucleotide according to the present invention, of a compound according to the present invention or of a pharmaceutical composition according to the present invention.

Finally, the present invention relates to the use of an antibody according to the present invention or of a compound according to the present invention as a research tool particularly suited to this study of signalling methods associated with the endothelin/endothelin receptor axis, as well as for progressing in understanding the structural and functional characteristics of this family of receptors.

Other features and advantages of the present invention will also be clear to a person skilled in the art from a reading of the following examples given by way of illustration and non-limitatively, with reference to the accompanying figures.

BRIEF DESCRIPTION OF THE DRAWINGS

FIG. 7 presents the results of in vivo fluorescence imaging on a preclinical nude mouse model xenografted in the orthotopical position with GLI-7 cells. FIG. 7A presents the positive control for detection of Rendomab A63-AF680 and of Control-AF750. FIG. 7B presents the detection of the in vivo fluorescence in the grafted mouse and the control mouse. FIG. 7C presents the detection of the ex vivo fluorescence in the grafted brain and the control brain.

FIG. 8 presents the nucleotide sequences and the amino acid sequences deduced from the variable domains of the light chain and of the heavy chain of Rendomab-A63.

DETAILED DISCLOSURE OF PARTICULAR EMBODIMENTS

I. Equipment and Methods

The strategy for immunisation and screening of the hybridomas used in the present invention is identical to that used in the international applications WO 2012/045776 [14] and WO 2017/220739 [15].

II. Biochemical Characterisation

After purification of the Rendomab-A63 on Protein A—PropSep high capacity (Millipore), characterisation of the biochemical properties thereof was carried out.

The isotyping of the heavy and light chains of the Rendomab-A63 was carried out using the "Rapid ELISA Mouse mAb Isotyping" kit from Piercell. This is type G immunoglobulin, of isotype 2b for the heavy chain and kappa for the light chain. Rendomab-A63 is therefore an immunoglobulin of type IgG2b/kappa.

Recognition of the ETA-R in its cell context (CHO-ETAR and Gli-7 cells) by Rendomab-A63 was established by flow cytometry and immunofluorescence cell marking.

The binding curves for Rendomab-A63 were produced
i) on the CHO (standing for "Chinese Hamster Ovary") cell line, not expressing ETA-R (CHO-WT),
ii) on the CHO-ETAR line, CHO cells, transfected in a stable manner, to allow strong expression of ETA-R, and
iii) on the line of glioblastoma cell strains, Gli-7, established by Dr Jean-Philippe Hugnot from a biopsy following exeresis of a glioblastoma in a patient.

The fluorescence is quantified by flow cytometry on an FACSCalibur™ (BD Bioscience). A range of concentrations of antibodies lying between, at a maximum, 1 µM and, at a minimum, 5 pM was incubated for 2 hours at 4° C. in the presence or not of 100 nM ET1 (preincubated for 30 minutes at 4° C.). At 90% confluence, the cells are detached in the presence of versene and then aliquoted in tubes (300 µl/300,000 cells) in the presence of a saturation buffer (PBS-SNC 5%-BSA 0.1%) stored at 4° C. After three washes in PBS buffer, 300 µl of secondary antibody labeled with Alexa Fluor™ 488 (AF-488) diluted to ¹⁄₄₀₀ was added and incubated for 60 minutes at 4° C. (Goat anti-mouse IgG, Invitrogen-ref A10684). For each antibody concentration point, after three washes in PBS, 10,000 cells were counted with flow cytometry.

Figure 1:
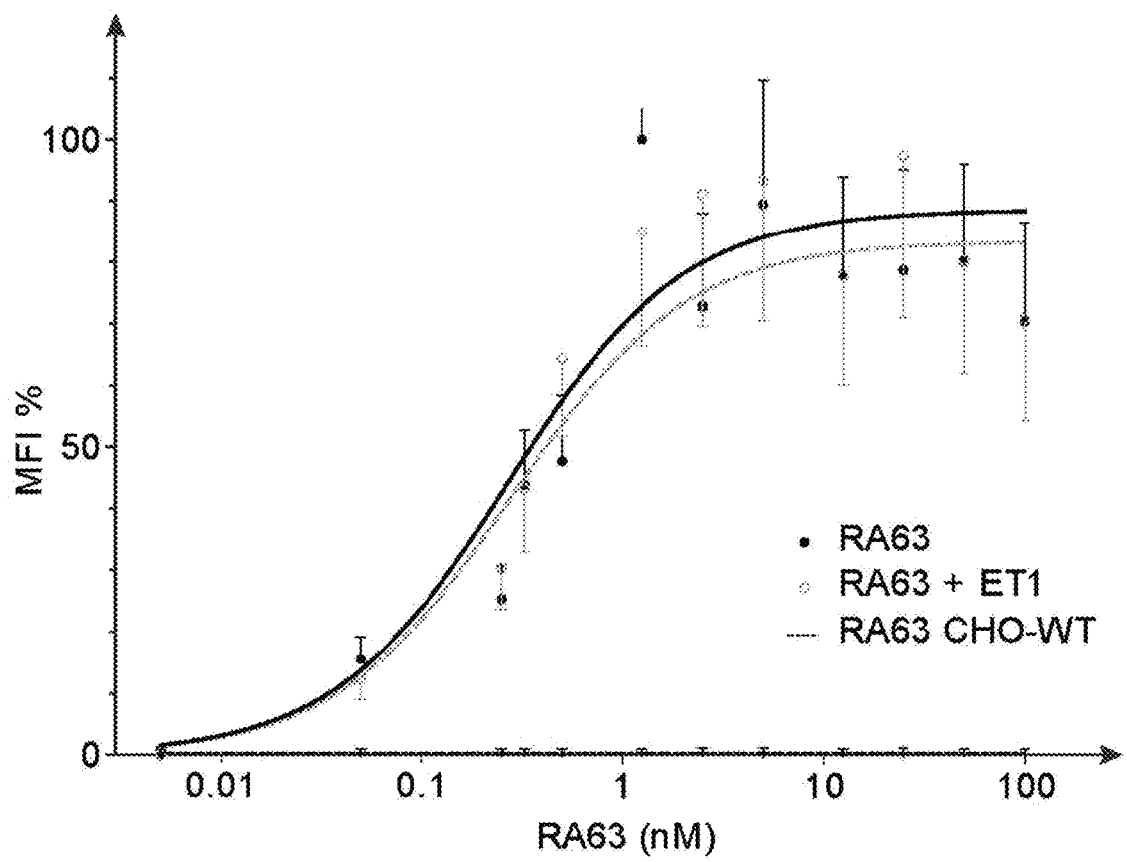
FIG. 1 presents the curves for bonding of Rendomab-A63 to CHO cells overexpressing ETA-R (CHO-ETAR) or CHO not expressing ETA-R (CHO-WT) in the presence or not of endothelin 1 (ET1).

The data were analysed in the GraphPad Prism software and the curves modelled according to the parameter: a specific binding site. The apparent dissociation constants calculated gave the values of Kd close to 0.5 nM on the CHO-ETAR line in the presence or not of ET1 (FIG. 1). The binding of RA63 was therefore not modified in the presence of ET1. In addition, the absence of binding of Rendomab-A63 on the CHO-WT cells was noted, thus demonstrating the binding specificity for ETA-R.

Figure 2:
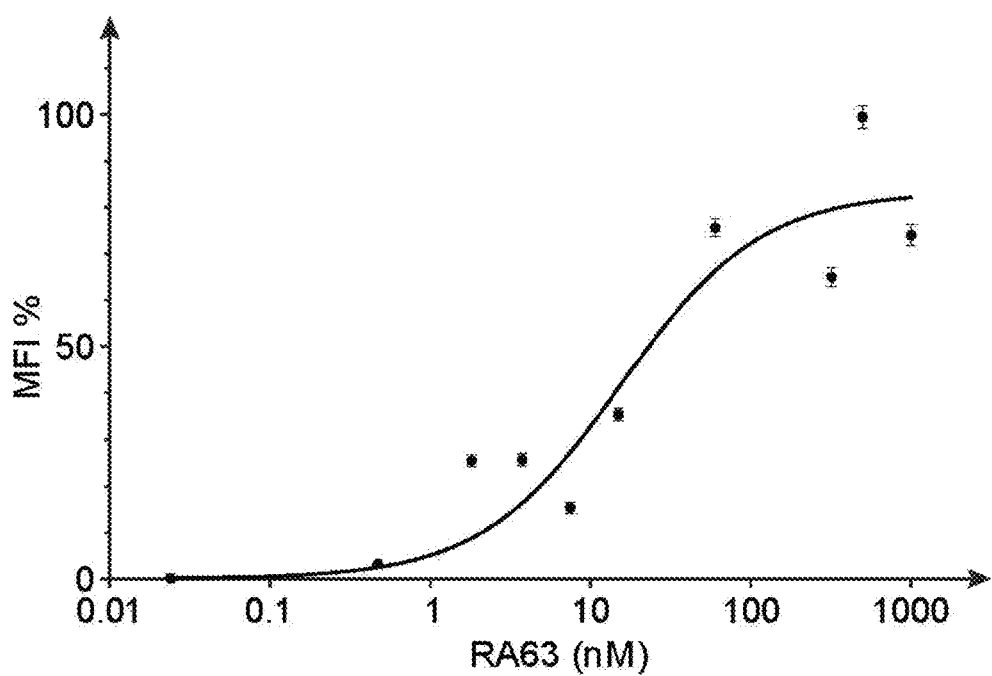
FIG. 2 presents the binding curves of Rendomab-A63 to glioblastoma strain cells, GLI-7, overexpressing ETA-R.

As illustrated in FIG. 2, the affinity of RA63 for ETA-R expressed on the surface of the Gli-7 cells is around one nanomolar (15 nM).

III. Immunofluorescence on Glioblastoma Gli-7 Strain Cells

III.1. Preliminary Remarks

Figure 3:
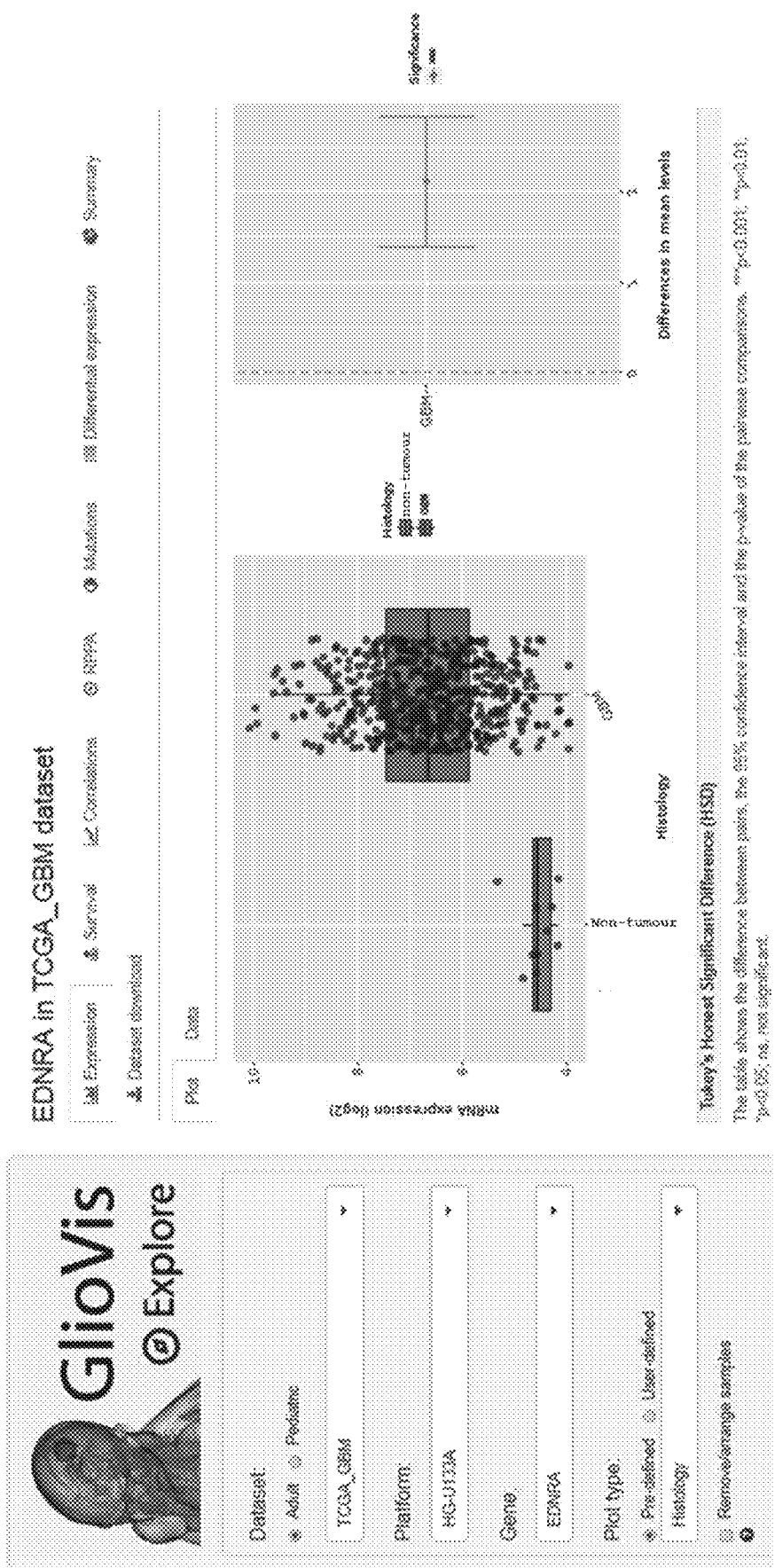
FIG. 3 presents the difference in the level of expression of the EDNRA transcript coding for the endothelin receptor A in glioblastoma cells in patients (denoted GBM) compared with non-tumoral neurone cells (denoted non-tumour).

Glioblastoma tumour cells are known for overexpressing ET-1 [20] and the endothelin type A receptor (ETAR) as shown by the transcriptomic data of the Gliovis public base presented in FIG. 3. These data indicate clearly an overexpression of the EDNRA transcript in the glioblastoma cells of the patients.

III.2. Results

Figure 4A:
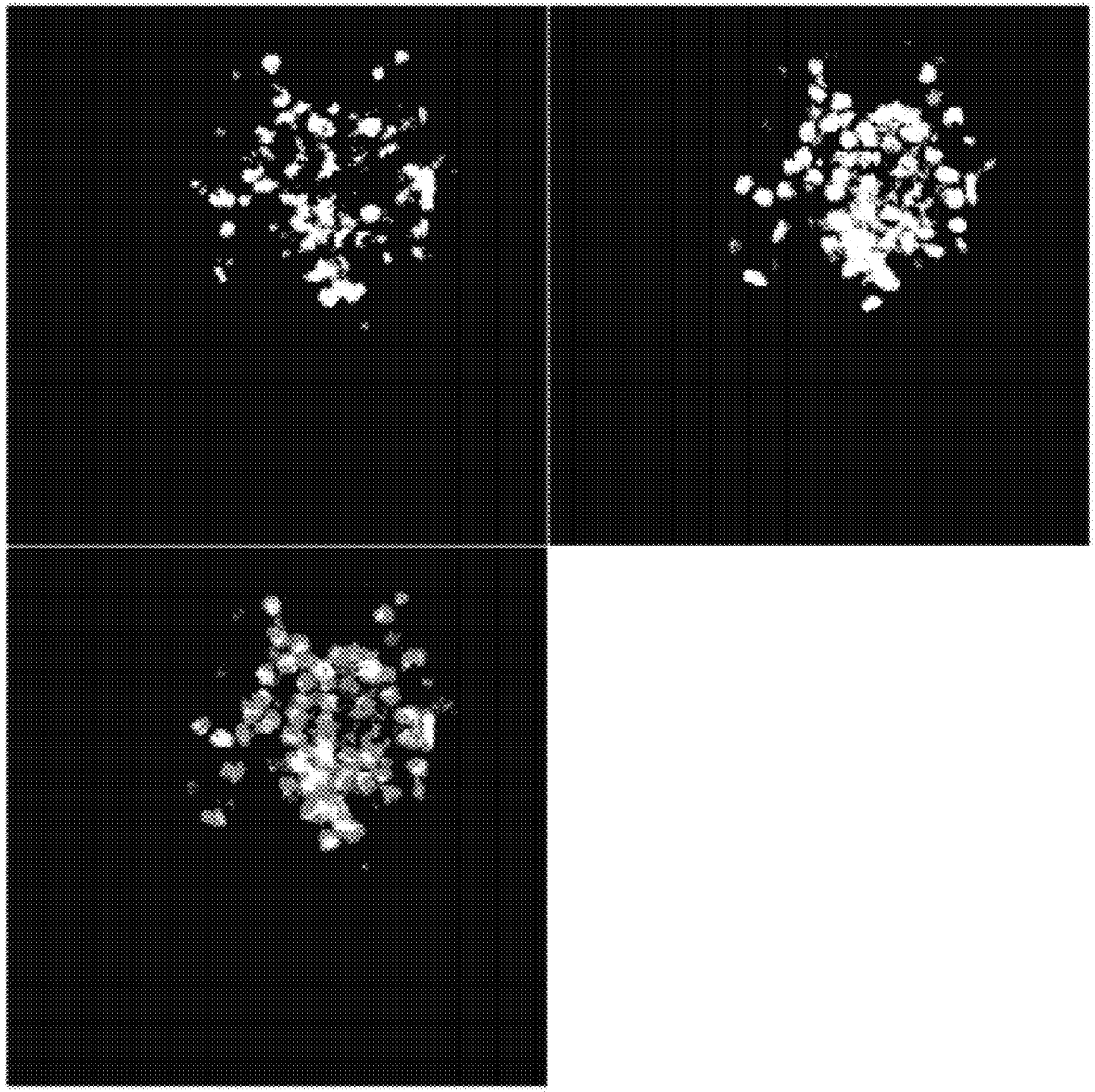
FIG. 4 presents results of immunofluorescence on glioblastoma GLI-7 strain cells, in the presence of 1 µM of ET1-FAM (FIG. 4A), in the presence of 30 nM of Rendomab-A63 (RA63) (FIG. 4B) or in the presence of 30 nM of a control antibody (NC) (FIG. 4C). The nuclei are coloured with DRAQ5.
Figure 4B:
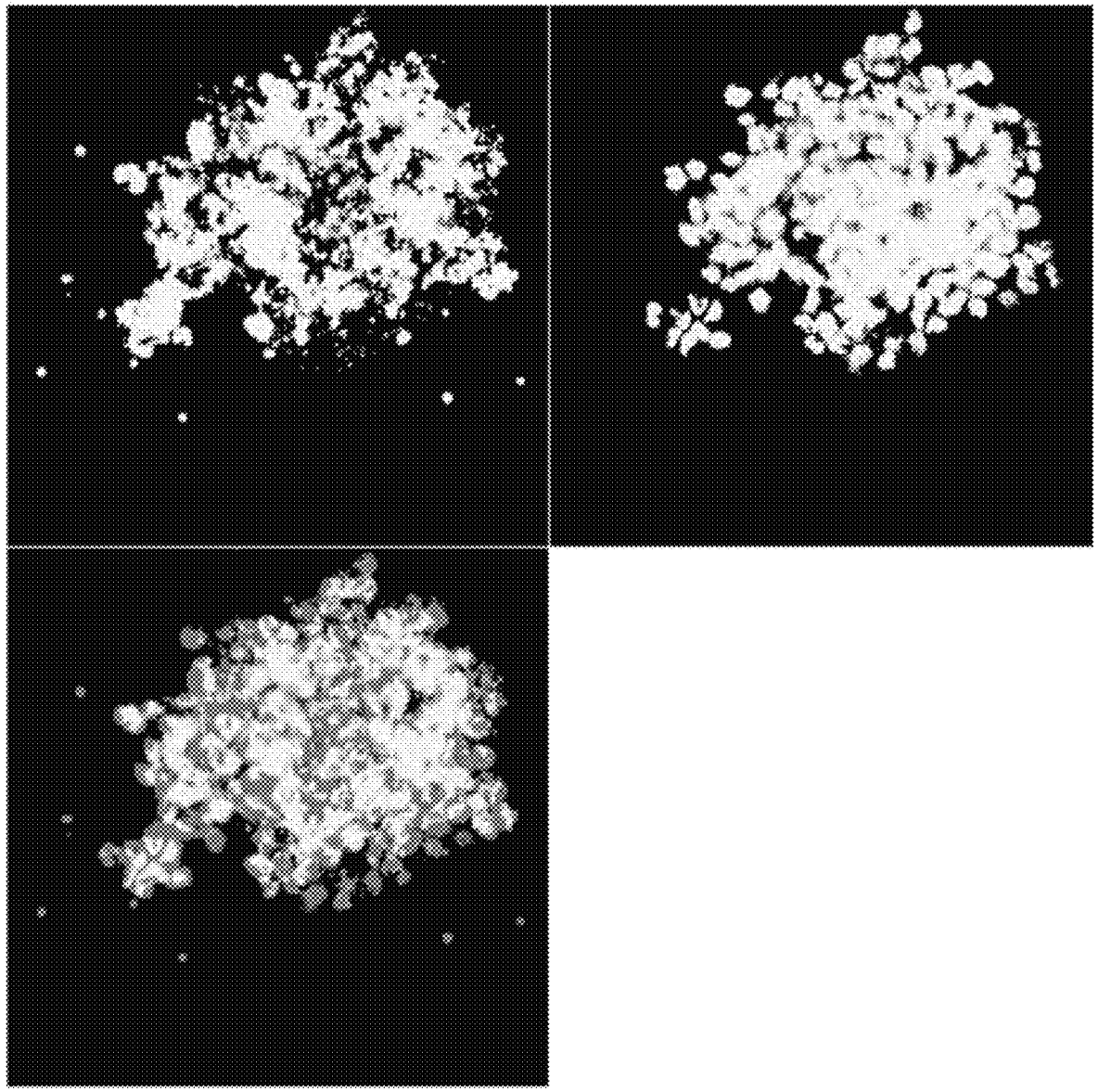
Figure 4C:
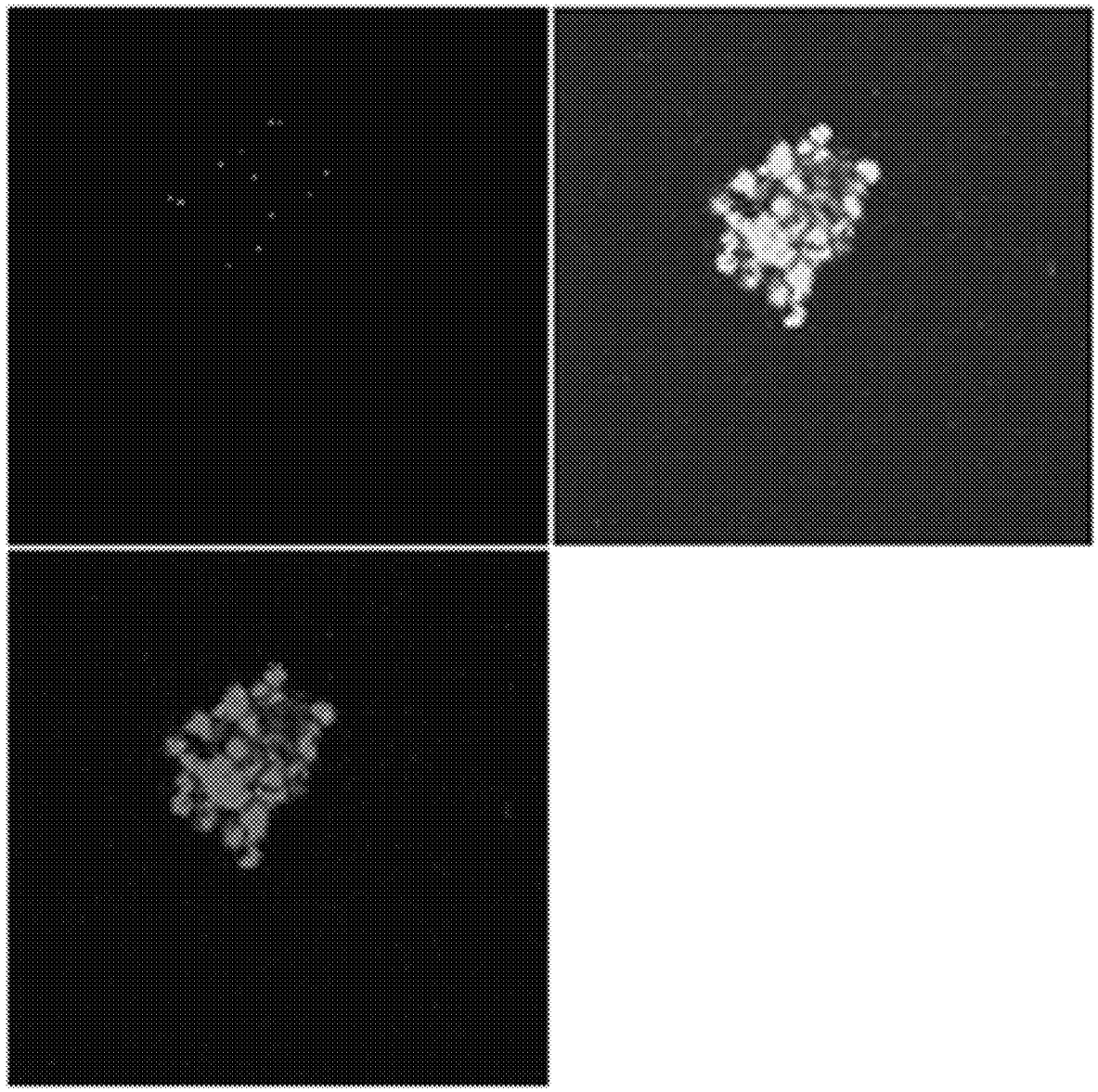

FIG. 4 presents results of immunofluorescence on the glioblastoma Gli-7 strain cells under the following operating conditions:

in the presence of 1 µM of ET1-FAM (Phoenix Pharmaceuticals FG-023-01A) (FIG. 4A);
in the presence of 30 nM of Rendomab-A63 (FIG. 4B); and
in the presence of 30 nM of a control antibody (NC) and of the same secondary antibody also diluted to 1/400 (FIG. 4C).

The nuclei are coloured with DRAQ5 (Abcam ab108410) following the protocol of the supplier. The Gli-7 cells were incubated for 12 hours at 4° C. with either 1 µM of ET1FAM, or 30 nM final of RA63, or 30 nM final of NC. After three washes with PBS, for the labeling with the antibodies, the secondary antibody is added, diluted to 1/400, coupled with AF488 (Invitrogen—ref A10684) to the cells for 2 hours at 4° C. After three washes with PBS, the cells were mounted in an aqueous medium, Aquatex® (VWR 1 08562 0050) on plates, in order to be observed under confocal microscope (ZEISS).

FIG. 4A makes it possible to ensure the presence of the endothelin receptors capable of binding endothelin 1 on the Gli-7 cells. FIG. 4B shows a very strong immune-labeling of the Gli-7 cells with the RA63 antibody recognising the endothelin receptor A, whereas a negative control antibody (NC), of the same isotype as RA63 (IgG2b Kappa), does not generate any signal on the Gli-7 cells (FIG. 4C). All these results make it possible to conclude that there is a strong expression of ETA-R on the surface of the Gli-7 cells revealed by the binding of the specific RA63 antibody of the ETA-R. This binding is well mediated by the variable region of the RA63 antibody, as shown by the absence of a signal when the control antibody is used.

III.3. Comparative Results

In the immunisation process that made it possible to generate the RA63 antibody according to the invention, a plurality of monoclonal antibodies were obtained.

Figure 5:
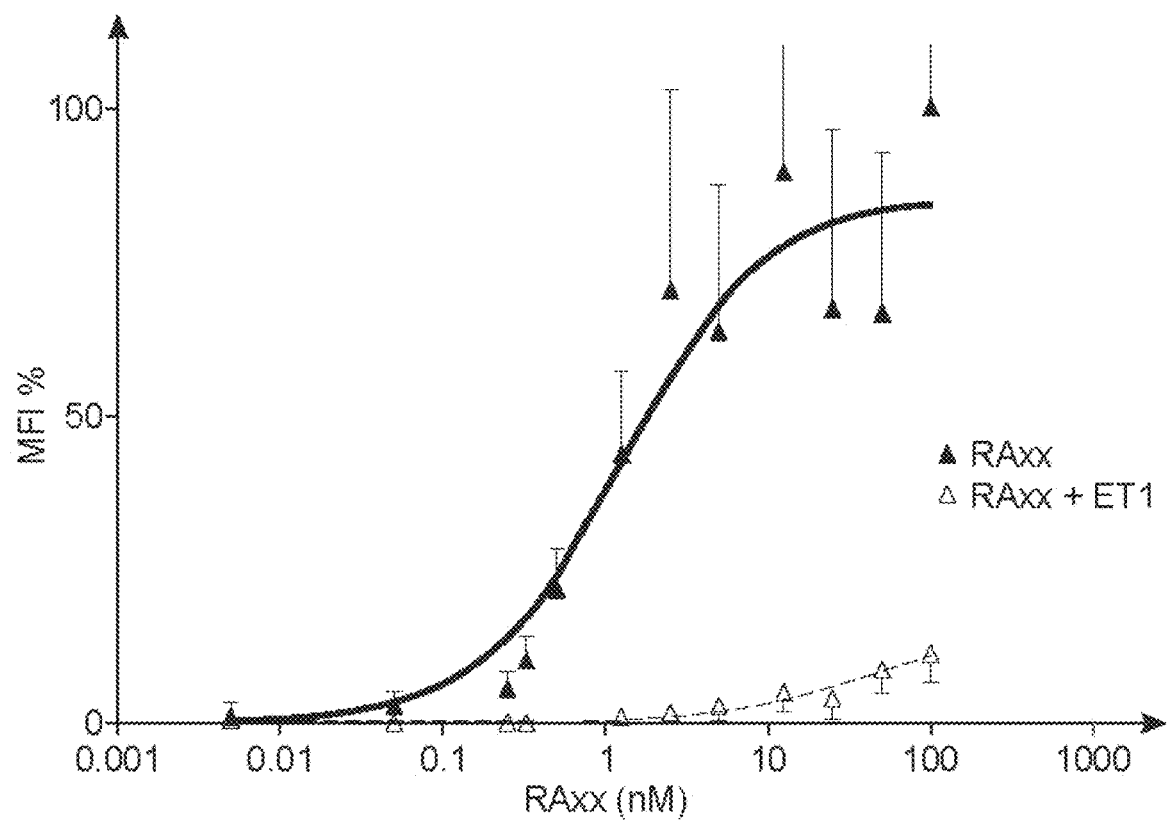
FIG. 5 presents the curve for bonding of the Rendomab Axx antibody, which does not form part of the invention, to CHO cells transfected with the endothelin type A receptor (CHO ETAR) (continuous black line) and in the presence of 100 nM of endothelin 1 (ET1) (broken grey line).

In particular, the Rendomab-Axx antibody directed against ETAR having an nM affinity but the binding of which on the endothelin receptor A is shifted by a concentration of 100 nm of ET1 (FIG. 5). This antibody therefore has properties comparable to those of the antibodies described in the patent application CA 2 971 491 [13].

Figure 6:
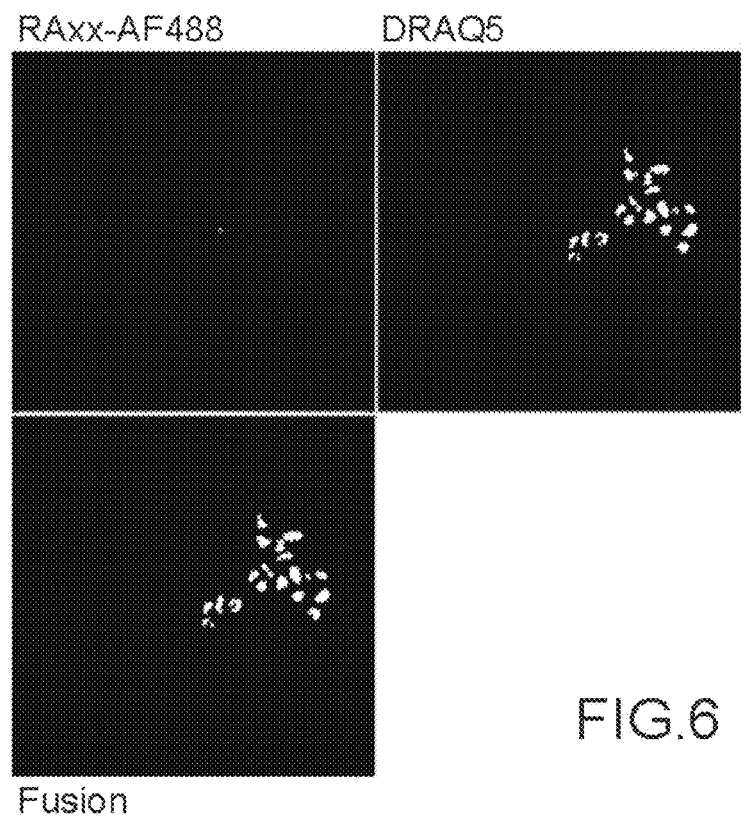
FIG. 6 presents the marking by immunofluorescence on the glioblastoma GLI-7 strain cells in the presence of 30 nM of Rendomab-Axx (RAxx) revealed by a secondary antibody labeled with Alexa fluor 488 (Raxx-AF488). The nuclei are coloured with DRAQ5. The two images are merged (Fusion).

This same antibody Raxx is not capable of binding to glioblastoma cells as shown by the immunofluorescence experiment presented in FIG. 6. This experiment demonstrates the existence of a conformation of the ETAR receptor present on the surface of the glioblastoma cells not recognised by the Raxx antibody but recognised by the RA63 antibody.

IV. In Vivo Imaging by Fluorescence Tomography on a Preclinical Animal Model

FIG. 7 presents the results of in vivo fluorescence imaging on a preclinical nude mouse model xenografted in the orthotopical position with Gli-7 cells.

For FIG. 7A, a range of quantities of RA-AF680 and NC-AF750 tracers were imaged on a solid FMT 1500 support (Perkin Elmer) in order to demonstrate the specificity of the filters used for detecting fluorescence, either i) at 680 nm where only the RA63-AF680 emits a detectable fluorescence signal, or ii) at 750 nm where only the NC-AF750 emits a detectable fluorescence signal.

For FIG. 7B, the mice are imaged at D0+3 months after xenografting. A co-injection of the RA63-AF680 tracers (14 nmols of RA63 coupled with 8 nmols of AF680) and NC-AF750 (17 nmols of control antibody coupled with 7 nmols of AF750) were injected by intraperitoneal route (IP) in the xenografted nude mouse and in the normal nude mouse (control mouse).

Ten days after IP injection, necessary for eliminating the tracers from the blood circulation, the mice were imaged with FMT 1500 (Perkin Elmer). For each mouse, a simultaneous acquisition at 680 nm and 750 nm was made. A strong fluorescence at 680 nm at the head of the xenografted mouse was observed, whereas, on this same mouse, the NC-AF750 tracer does not generate any fluorescence at 750 nm. Thus only the RA63-AF680 tracer was detected on the xenografted living mouse with the GLI-7 line. The absence of detection of the RA63-AF680 and NC-AF750 injected into the normal mouse was also noted.

For FIG. 7C, the mice were sacrificed, their brain removed and fixed with a 4% paraformaldehyde solution (PFA 4%) for 1 hour at 4° C. The brains were imaged as before. Once again a strong fluorescence with the RA63-AF680 tracer was observed in the brain invaded by the tumour cells, whereas no signal is detected with the NC-AF750 tracer. The absence of fluorescence is also found with the two tracers RA63-AF680 and NC-AF750 in the brain of the control mouse.

In conclusion, the RA63 antibody can be used as a tracer (RA63-AF680), for diagnosing the presence of glioblastoma tumour cells (Gli-7) for imaging applications.

V. Molecular Cloning

Cloning of the nucleic transcripts coding the heavy chain and the light chain of Rendomab-A63, was performed using the kits: "GenElute/Total RNA" (Sigma-Aldrich) and "RACE-PCR" (Invitrogen).

The deduced nucleic amino acid sequences of the variable domains of the light chain (VL) and of the heavy chain (VH) of Rendomab-A63 are presented in FIG. 8.

BIBLIOGRAPHIC REFERENCES

[1] Bulenger et at 2005, "Emerging role of homo- and heterodimerization in G-protein-coupled receptor biosynthesis and maturation", Trends Pharmacol. Sci., vol. 26, pages 131-137.

[2] Kenakin & Miller, 2010, "Seven Transmembrane Receptors as Shapeshifting Proteins: The Impact of Allosteric Modulation and Functional Selectivity on New Drug Discovery", Pharmacol. Rev., vol. 62, pages 265-304.

[3] Hilger et al, 2018, "Structure and dynamics of GPCR signaling complexes", Nat. Struct. Mol. Biol., vol. 25, pages 4-12.

[4] Shihoya et al, 2016, "Activation mechanism of endothelin $ET_B$ receptor by endothelin-1", Nature, vol. 537, page 363

[5] Bagnato & Rosanó, 2008, "The endothelin axis in cancer", Int. J. Biochem. Cell Biol., vol. 40, pages 1443-1451.

[6] Rosanó et al, 2013, "Endothelin 1 in cancer: biological implications and therapeutic opportunities", Nat. Rev. Cancer, vol. 13, pages 637-651.

[7] Allard et at 2013, "Generation and characterization of rendomab-B1, a monoclonal antibody displaying potent and specific antagonism of the human endothelin B receptor", mAbs, vol. 5, pages 56-69.

[8] Borrull et al, 2016, "Rendomab B4, a monoclonal antibody that discriminates the human endothelin B receptor of melanoma cells and inhibits their migration", mAbs, vol. 8, pages 1371-1385.

[9] Cazaubon et al, 2006, "Endothelin-1 angiotensin II and cancer», Médecine/Sciences, vol. 22, pages 416-422.

[10] Shah, 2007, "Endothelins in health and disease", Eur. J. Int. Med., vol. 18, pages 272-282.

[11] Irani et al, 2014, "A review of the profile of endothelin axis in cancer and its management", Critical Reviews in Oncology/Hematology, vol. 89, pages 314-321.

[12] Kondoh et al, 1990, "Isolation of anti-endothelin receptor monoclonal antibodies for use in receptor characterization", BBRC, vol. 172, pages 503-510.

[13] Patent application CA 2 971 491 in the name of Gmax Biopharm LLC, published on 8 Jun. 2017.

[14] International application WO 2012/045776 in the name of the Commissariat à l'Energie Atomique et aux Energies Alternatives, published on 12 Apr. 2012.

[15] International application WO 2017/220739 in the name of the Commissariat à l'Energie Atomique et aux Energies Alternatives, published on 28 Dec. 2017.

[16] Verhoeyen et al, 1988, "Reshaping human antibodies: Grafting an antilysozyme activity", Science, vol. 239, pages 1534-1536.

[17] Patent U.S. Pat. No. 4,816,567 in the name of Genentech, published on 28 Mar. 1989.

[18] Vaughan et al, 1998, "Human antibodies by design", Nature Biotechnol. vol. 16, pages 535-539.

[19] Sambrook et al, 1989, Molecular cloning, Noland C. ed., New York: Cold Spring Harbor Laboratory Press.

[20] Egidy et al, 2000, "The endothelin system in human glioblastoma", Lab. Investig. J. Tech. Methods Pathol., vol. 80, pages 1681-1689.

The invention claimed is:

1. An antibody directed against the endothelin receptor subtype A having:
   i) at least one light-chain variable region, wherein the amino acid sequence:
      of the CDR1$_L$ is SQSIVYSNGKIYL (SEQ ID NO: 2);
      of the CDR2$_L$ is KVS;
      of the CDR3$_L$ is FQGSHLPLT (SEQ ID NO: 4); and
   ii) at least one heavy-chain variable region wherein the amino acid sequence;
      of the CDR1$_H$ is GFTFNIYA (SEQ ID NO: 6);
      of the CDR2$_H$ is IRSKSNNYAT (SEQ ID NO: 8);
      of the CDR3$_H$ is VSSYYSGSFFAY (SEQ ID NO: 10);
   a fragment or a derivative thereof,
   wherein said fragment has at least one antigen-binding site, and
   wherein said derivative being a single chain Fv or a single domain antibody.

2. The antibody according to claim 1, wherein said antibody comprises at least one light-chain variable region wherein the amino acid sequence has at least 60% identity with the following sequence:

(SEQ ID NO: 12)
DVLMTQTPLSLPVSLGDQASISCRSSQSIVYSNGKIYLEWYLQKPGQSPKL

LIYKVSNRFSGVPDRFSGSGSGTDFTLKISRVEAEDLGVYYCFQGSHLPLT

FGAGTKLELKR.

3. The antibody according to claim 1, wherein said antibody comprises at least one heavy-chain variable region wherein the amino acid sequence has at least 60% identity with the following sequence:

(SEQ ID NO: 14)
EVQLVESGGGLVQPKGSLKLSCAASGFTFNIYAMNWIRQAPGKGLEWIARI

RSKSNNYATYYADSVKDRFTISRDDSQNMVYLQMNNLKTEDTAMYYCVSSY

YSGSFFAYWGQGTLVTVSA.

4. The antibody according to claim 1, wherein said antibody is an immunoglobulin of type IgG2b/kappa.

5. The antibody according to claim 1, wherein said antibody is monoclonal.

6. The antibody according to claim 1, wherein said antibody is the monoclonal murine antibody obtained from the hybridoma filed at the CNCM on 18 Oct. 2017 under the number CNCM I-5250.

7. The antibody according to claim 1, wherein said antibody is a chimerised antibody.

8. The antibody according to claim 1, wherein said antibody is a humanised antibody.

9. An isolated polynucleotide chosen from the following various polynucleotides:
   (a) a polynucleotide coding an antibody as defined in claim 1;
   (b) a polynucleotide that is complementary to the polynucleotide as defined at point (a); and
   (c) a polynucleotide of at least 18 nucleotides, capable of hybridising under high-stringency conditions to the polynucleotides as defined at points (a) and (b).

10. A cloning and/or expression vector containing at least one polynucleotide according to claim 9.

11. A host organism transformed by or comprising a polynucleotide according to claim 9 or a vector according to claim 10.

12. A compound comprising an antibody according to claim 1 conjugated with an element chosen from the group consisting of a cytotoxic group, a group detectable by microscopy, scintigraphy or magnetic resonance imaging, or an effector group selected from the group consisting of an antibody identical to or different from the antibody according to claim 1, a protein, a peptide, a DNA, an RNA, an RNAi, an aptamer, a PNA and an LNA.

13. A method for diagnosing glioblastoma in vitro comprising the steps of:
   (i) putting a biological sample of a subject in contact with a compound according to claim 12;
   (ii) detecting a signal emitted by the group detectable by microscopy, scintigraphy or magnetic resonance imaging, and
   (iii) determining a presence or absence of a glioblastoma in said subject on the basis of the signal detected at step (ii) optionally compared with a control signal.

14. A pharmaceutical composition comprising, as active principle, an antibody according to claim 1 and a pharmaceutically acceptable vehicle.

15. A method for treating a cancer associated with ETAR overexpression, which method comprises administering to a subject in need thereof a compound comprising the antibody, the fragment or the derivative thereof according to claim 1, wherein said antibody, said fragment or said derivative thereof is conjugated with a cytotoxic group, and
   wherein said cancer is selected in the group consisting of colorectal cancer, colon cancer, Kaposi's sarcoma, a glioblastoma, ovarian cancer and bladder cancer.

16. The method according to claim 15, wherein said cancer is a glioblastoma.

17. A hybridoma filed at the CNCM on 18 Oct. 2017 under the number CNCM I-5250.

* * * * *

SEQUENCE LISTING

```
<160> NUMBER OF SEQ ID NOS: 14

<210> SEQ ID NO 1
<211> LENGTH: 39
<212> TYPE: DNA
<213> ORGANISM: Mus musculus
<220> FEATURE:
<221> NAME/KEY: CDS
<222> LOCATION: (1)..(39)
<223> OTHER INFORMATION: CDR1 of the light-chain variable region of
      Rendomab-A63

<400> SEQUENCE: 1 agt cag agc att gta tat agt aat gga aaa atc tat tta            39
Ser Gln Ser Ile Val Tyr Ser Asn Gly Lys Ile Tyr Leu
1               5                   10

<210> SEQ ID NO 2
<211> LENGTH: 13
<212> TYPE: PRT
<213> ORGANISM: Mus musculus

<400> SEQUENCE: 2

Ser Gln Ser Ile Val Tyr Ser Asn Gly Lys Ile Tyr Leu
1               5                   10

<210> SEQ ID NO 3
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: CDR3 of the light-chain variable region of
      Rendomab-A63

<400> SEQUENCE: 3 ttt caa ggt tca cat ctt ccg ctc acg                            27
Phe Gln Gly Ser His Leu Pro Leu Thr
1               5

<210> SEQ ID NO 4
<211> LENGTH: 9
<212> TYPE: PRT
<213> ORGANISM: Mus musculus

<400> SEQUENCE: 4

Phe Gln Gly Ser His Leu Pro Leu Thr
1               5
```

```
<210> SEQ ID NO 5
<211> LENGTH: 24
<212> TYPE: DNA
<213> ORGANISM: Mus musculus
<220> FEATURE:
<221> NAME/KEY: CDS
<222> LOCATION: (1)..(24)
<223> OTHER INFORMATION: CDR1 of the heavy-chain variable region of
      Rendomab-A63

<400> SEQUENCE: 5 gga ttc acc ttc aat atc tac gcc                              24
Gly Phe Thr Phe Asn Ile Tyr Ala
1               5

<210> SEQ ID NO 6
<211> LENGTH: 8
<212> TYPE: PRT
<213> ORGANISM: Mus musculus

<400> SEQUENCE: 6

Gly Phe Thr Phe Asn Ile Tyr Ala
1               5

<210> SEQ ID NO 7
<211> LENGTH: 30
<212> TYPE: DNA
<213> ORGANISM: Mus musculus
<220> FEATURE:
<221> NAME/KEY: CDS
<222> LOCATION: (1)..(30)
<223> OTHER INFORMATION: CDR2 of the heavy-chain variable region of
      Rendomab-A63

<400> SEQUENCE: 7 ata aga agt aaa agt aat aat tat gca aca                      30
Ile Arg Ser Lys Ser Asn Asn Tyr Ala Thr
1               5                   10

<210> SEQ ID NO 8
<211> LENGTH: 10
<212> TYPE: PRT
<213> ORGANISM: Mus musculus

<400> SEQUENCE: 8

Ile Arg Ser Lys Ser Asn Asn Tyr Ala Thr
1               5                   10

<210> SEQ ID NO 9
<211> LENGTH: 36
<212> TYPE: DNA
<213> ORGANISM: Mus musculus
<220> FEATURE:
<221> NAME/KEY: CDS
<222> LOCATION: (1)..(36)
<223> OTHER INFORMATION: CDR3 of the heavy-chain variable region of
      Rendomab-A63

<400> SEQUENCE: 9 gtg agt tcc tat tac tcc ggt agt ttc ttt gct tac              36
Val Ser Ser Tyr Tyr Ser Gly Ser Phe Phe Ala Tyr
1               5                   10

<210> SEQ ID NO 10
<211> LENGTH: 12
<212> TYPE: PRT
<213> ORGANISM: Mus musculus
```

<400> SEQUENCE: 10

Val Ser Ser Tyr Tyr Ser Gly Ser Phe Phe Ala Tyr
1               5                   10

<210> SEQ ID NO 11
<211> LENGTH: 339
<212> TYPE: DNA
<213> ORGANISM: Mus musculus
<220> FEATURE:
<221> NAME/KEY: CDS
<222> LOCATION: (1)..(339)
<223> OTHER INFORMATION: Light-chain variable region of Rendomab-A63

<400> SEQUENCE: 11

```
gat gtt ttg atg acc caa act cca ctc tcc ctg cct gtc agt ctt gga        48
Asp Val Leu Met Thr Gln Thr Pro Leu Ser Leu Pro Val Ser Leu Gly
1               5                   10                  15 gat caa gcc tcc atc tcg tgc aga tct agt cag agc att gta tat agt        96
Asp Gln Ala Ser Ile Ser Cys Arg Ser Ser Gln Ser Ile Val Tyr Ser
                20                  25                  30 aat gga aaa atc tat tta gaa tgg tac ctg cag aaa cca ggc cag tct       144
Asn Gly Lys Ile Tyr Leu Glu Trp Tyr Leu Gln Lys Pro Gly Gln Ser
        35                  40                  45 cca aag ctc cta atc tac aaa gtt tcc aac cga ttt tct ggg gtc cca       192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc       240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt       288
Ser Arg Val Glu Ala Glu Asp Leu Gly Val Tyr Tyr Cys Phe Gln Gly
                85                  90                  95 tca cat ctt ccg ctc acg ttc ggt gct ggg acc aag ctg gag ctg aaa       336
Ser His Leu Pro Leu Thr Phe Gly Ala Gly Thr Lys Leu Glu Leu Lys
            100                 105                 110 cgg                                                                   339
Arg
```

<210> SEQ ID NO 12
<211> LENGTH: 113
<212> TYPE: PRT
<213> ORGANISM: Mus musculus

<400> SEQUENCE: 12

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
                20                  25                  30

Asn Gly Lys Ile Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Ala Gly Thr Lys Leu Glu Leu Lys
            100                 105                 110

Arg

<210> SEQ ID NO 13
<211> LENGTH: 363
<212> TYPE: DNA
<213> ORGANISM: Mus musculus
<220> FEATURE:
<221> NAME/KEY: CDS
<222> LOCATION: (1)..(363)
<223> OTHER INFORMATION: Heavy-chain variable region of Rendomab-A63

<400> SEQUENCE: 13

```
gag gtg cag ctt gtt gag tct ggt gga gga ttg gtg cag cct aaa ggg      48
Glu Val Gln Leu Val Glu Ser Gly Gly Gly Leu Val Gln Pro Lys Gly
1               5                   10                  15 tca ttg aaa ctc tca tgt gca gcc tct gga ttc acc ttc aat atc tac      96
Ser Leu Lys Leu Ser Cys Ala Ala Ser Gly Phe Thr Phe Asn Ile Tyr
            20                  25                  30 gcc atg aac tgg atc cgc cag gct cca gga aag ggt ttg gaa tgg att     144
Ala Met Asn Trp Ile Arg Gln Ala Pro Gly Lys Gly Leu Glu Trp Ile
        35                  40                  45 gct cgc ata aga agt aaa agt aat aat tat gca aca tat tat gcc gat     192
Ala Arg Ile Arg Ser Lys Ser Asn Asn Tyr Ala Thr Tyr Tyr Ala Asp
    50                  55                  60 tca gtg aaa gac agg ttc acc atc tcc aga gat gat tca cag aat atg     240
Ser Val Lys Asp Arg Phe Thr Ile Ser Arg Asp Asp Ser Gln Asn Met
65                  70                  75                  80 gtc tat ctg caa atg aac aac ttg aaa act gag gac aca gcc atg tat     288
Val Tyr Leu Gln Met Asn Asn Leu Lys Thr Glu Asp Thr Ala Met Tyr
                85                  90                  95 tac tgt gtg agt tcc tat tac tcc ggt agt ttc ttt gct tac tgg ggc     336
Tyr Cys Val Ser Ser Tyr Tyr Ser Gly Ser Phe Phe Ala Tyr Trp Gly
            100                 105                 110 caa ggg act ctg gtc act gtc tct gca                                  363
Gln Gly Thr Leu Val Thr Val Ser Ala
        115                 120
```

<210> SEQ ID NO 14
<211> LENGTH: 121
<212> TYPE: PRT
<213> ORGANISM: Mus musculus

<400> SEQUENCE: 14

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Ile Tyr
            20                  25                  30

Ala Met Asn Trp Ile Arg Gln Ala Pro Gly Lys Gly Leu Glu Trp Ile
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Val Tyr Leu Gln Met Asn Asn Leu Lys Thr Glu Asp Thr Ala Met Tyr
                85                  90                  95

Tyr Cys Val Ser Ser Tyr Tyr Ser Gly Ser Phe Phe Ala Tyr Trp Gly
            100                 105                 110

Gln Gly Thr Leu Val Thr Val Ser Ala
        115                 120
```